(12) United States Patent
Fromer et al.

(10) Patent No.: US 7,179,954 B1
(45) Date of Patent: Feb. 20, 2007

(54) ISOLATED NUCLEIC ACIDS CODING FOR A NUCLEAR BASE TRANSPORTER AND USES THEREOF

(75) Inventors: Wolf B. Fromer, Tübingen (DE); Bernd Gillissen, Berlin (DE); Lukas Bürkle, Keltern (DE); Bruno Andre, Brussels (BE)

(73) Assignee: Carnegie Insitution of Washington, Washington, DC (US)

( * ) Notice: Subject to any disclaimer, the term of this patent is extended or adjusted under 35 U.S.C. 154(b) by 0 days.

(21) Appl. No.: 09/913,767

(22) PCT Filed: Feb. 21, 2000

(86) PCT No.: PCT/EP00/01397

§ 371 (c)(1),
(2), (4) Date: Jan. 10, 2002

(87) PCT Pub. No.: WO00/49152

PCT Pub. Date: Aug. 24, 2000

(30) Foreign Application Priority Data

Feb. 19, 1999 (DE) ................................ 199 07 209

(51) Int. Cl.
*C12N 15/09* (2006.01)
*C12N 15/82* (2006.01)
*C12N 15/29* (2006.01)
*A01H 5/00* (2006.01)

(52) U.S. Cl. ...................... 800/278; 800/298; 435/468; 435/320.1; 435/69.1

(58) Field of Classification Search ............... 536/23.6, 536/23.7, 23.2; 435/69.1, 468, 320.1; 800/278, 800/298, 286, 288, 295
See application file for complete search history.

(56) References Cited

U.S. PATENT DOCUMENTS 5,719,043 A * 2/1998 Frommer .................. 435/69.1
6,551,796 B1 * 4/2003 Abramson et al. ......... 435/69.1

FOREIGN PATENT DOCUMENTS

WO      WO 98/29437       7/1998

OTHER PUBLICATIONS

Chen et al. Plant Physiology, vol. 125, pp. 1813-1820 (2001).*
Schultes et al. The Plant Cell (1996), vol. 8, pp. 463-475.*
Gillissen et al. The plant Cell (2000), vol. 12, pp. 291-300.*
Burkle et al. The Plant Journal (2003), vol. 34, pp. 19-26.*
Pjura et al. Protein Science, 1993, 2:2217-2225.*
Uppaluri et al. Mol. Cell. Biol., 1995, pp. 1499-1512.*
Kim et al. J. Biol. Chem. 1996, 271(9): 4872-78.*
Griffiths, et al., "Cloning of a human nucleoside transporter implicated in the cellular uptake of adenosine and chemotherapeutic drugs," *Nature Medicine*, 3(1):89-93 (Jan. 1997).
Gillissen,et al.; "A New Family of High-Affinity Transporters for Adenine, Cytosine, and Purine Derivatives in *Arabidopsis,*" *The Plant Cell*, 12:291-300 (Feb. 2000).
Bevan et al., "*A. thaliana* chromosome 4; AC AL021713", EBI Database, Biological Sequence ID No. ATT9A21 (submitted Sep. 22, 1999 to EMBL/GenBank/DDBJ Databases; created Feb. 3, 1998).
Lin et al., "*A. thaliana* chromosome 2 fragment; AC U78721, P93010," EBI Database, Biological Sequence ID Nos. U78721 (submitted Dec. 13, 1999 to EMBL/GenBank/DDBJ Databases; Created Dec. 13, 1996) and P93010 (submitted Dec. 1996 to EMBL,/GenBank/DDBJ Databases).
Newman et al., "*Arabidopsis* EST AC H76984," EBI Database, Biological Sequence Accession No. AT98416 (created Nov. 10, 1995).
Schultes, et al., "*Leaf permeasel* Gene of Maize is Required for Chloroplast Development," *The Plant Cell*, 8:463-475, (Mar. 1996).
Sentenac, et al., "Cloning and Expression in Yeast of a Plant Potassium Ion Transport System," *Science*, 256:663-665 (May 1, 1992).
Frommer et al., Seed and vascular expression of a high-affinity transporter for cationic amino acids in *Arabidopsis*, Proc. Natl. Acad. Sci. USA, 92:12036-12040 (Dec. 1995).
Detke, Cloning of the *Candida albicans* nucleoside transporter by complementation of nucleoside transport-deficient *Saccharomyces*, Abstract from Yeast, 14:1257-65 (Oct. 1998).

* cited by examiner

*Primary Examiner*—Medina A. Ibrahim
(74) *Attorney, Agent, or Firm*—Morgan Lewis & Bockius LLP

(57) ABSTRACT

The invention concerns nucleic acids coding for *Arabidopsis* nuclear base transporter, DNA constructs and host cells containing the nucleic acids. The invention also concerns methods of transforming plants and host cells with nuclear base transporter encoding nucleic acids. Transgenic plants, plant cells, and seeds expressing nuclear base transporter are also disclosed.

25 Claims, 8 Drawing Sheets

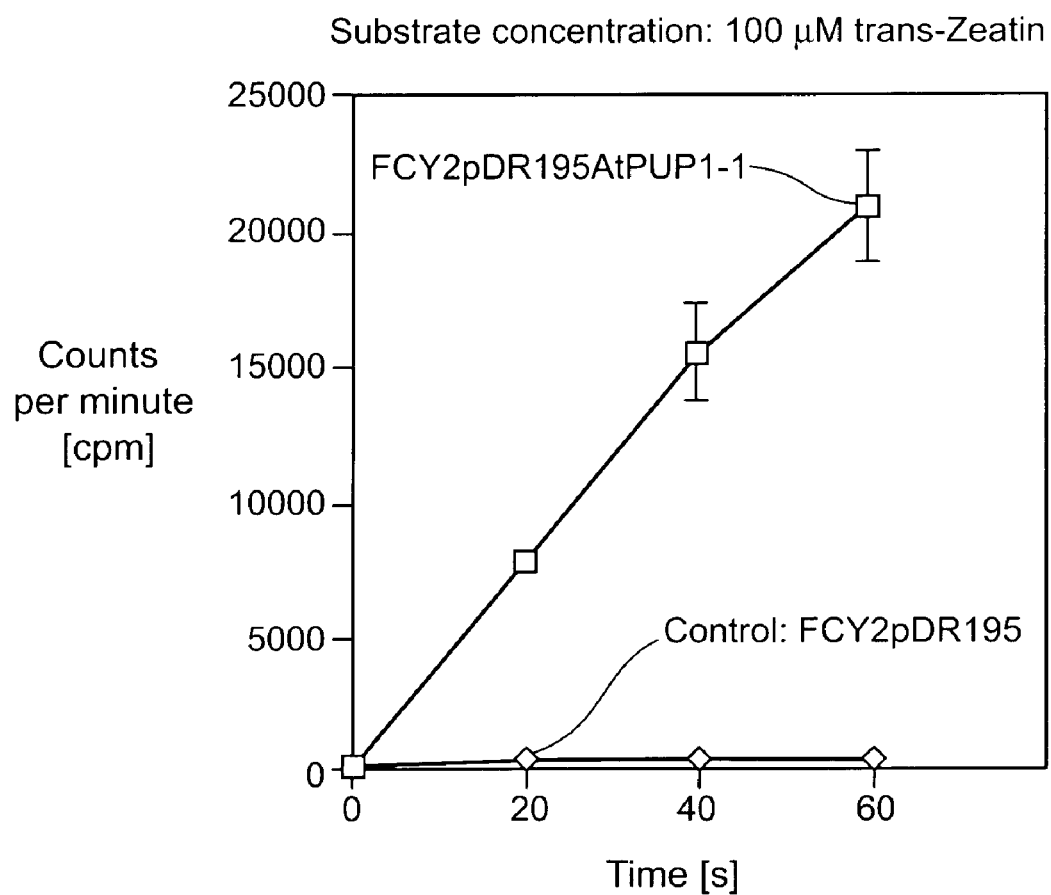

SEQUENCE LISTING

```
<160> NUMBER OF SEQ ID NOS: 13

<210> SEQ ID NO 1
<211> LENGTH: 1225
<212> TYPE: DNA
<213> ORGANISM: Arabidopsis thaliana

<400> SEQUENCE: 1
aaaacagcaa gcagcaagaa gaagatgaag aatggtttga taatcataaa ctgtattatc      60
ctcactatag gaacatgtgg aggtcctttg ttaactcgtc tctacttcac caatggcgga     120
aaacgaatct ggttcatgag cttcctatca accgctggtt ttccaatcat cctcatccct     180
ctcttggtct ccttcctcag ccgtcgccgc ggcaaccgca accctaacaa cgcggaaaac     240
aagcggaaaa caaagctctt cctcatggaa actcctctgt ggagcgcctc cattgtcata     300
gggttgctca caggacttga caactactta tattcttacg gattagcata tctgccagtt     360
tcaacttcat cgctcataat cggaactcaa ctagctttca acgctctctt cgctttcttg     420
ttagtcaagc aaaagttcac tccgttctcc ataaacgccg tcgtttttgtt gacggttggt     480 atcgggatcc ttgcgttaca cagtgatgga gacaaaccgg ctaaggagag caagaaagag     540
tatgtggttg ggttcttgat gactgtggtt gcagctcttc tctatgcttt tatattaccg     600
ctcgttgagc taacttacaa gaaagctcgt caagaaatca ctttcccact tgtgcttgag     660
attcagatgg tcatgtgcct tgctgctact tttttctgtg tcattggcat gttcatcgtt     720
ggagatttta aggtgatagc aagagaagca agagagttca agattggagg atcagtgttt     780
tactatgcat tgatagtgat cacaggaata atatggcaag gtttcttctt aggagccata     840
gggattgtgt tttgtgcatc atcactagct tctggtgttc tgataagtgt tctgcttccg     900
gtgactgaag ttttcgccgt cgtttgtttc cgggagaagt tcaggcaga gaaaggtgtc     960 tctctacttc tttctctttg gggatttgtc tcttacttct acggcgagtt taaatccggc    1020
aagaaagttg ttgataaacc tcaaccgccg gagacagaac tgcctattct tccagttagt    1080
```

-continued

| gattatgttg cttaatttct ataactctat acgattataa cagagcatta ctgttatgtt | 1140 |
| ttgttcctaa atattatgtg tgattgtgtg tttttgttat tgttcttgtg tataagtatg | 1200 |
| aataaaattt gaaagatatt gagct | 1225 |

<210> SEQ ID NO 2
<211> LENGTH: 1049
<212> TYPE: DNA
<213> ORGANISM: Arabidopsis thaliana

<400> SEQUENCE: 2

| aagatgaaga tgaagacagt tcttgtaatc ataaactgta tattcttggc cattggaaac | 60 |
| tgtggaggcc ctctaatgat gcgtctctac ttccaaaatg gtggcgaaag gatctggttt | 120 |
| ccaagcttcc ttcaaaccgt tggttgtcca ctcattttct tccctcttct cttatctttc | 180 |
| ctccgccgtc gtcgttgcct tgaagaacaa gaaacgactc cattttttcct catgaaacct | 240 |
| cctctcttta tcgccgctat cgttgttggt ttgctcgtgg gatttgacaa ttacctctac | 300 |
| tcttacgggt tagcttatat ccctgtttct actgcgtctt tgatcatctc cgcgcaatta | 360 |
| ggcttcactg ctctctttgc atttttttatg gtgaagcaaa agttcacacc tttcactata | 420 |
| aacgctatcg ttttgctcac tggtggtgcc gtagtccttg cccttaactc tgatagtgac | 480 |
| aagcttgcaa acgagacaca caaggaatat gttgttgggt tcatcatgac tcttggtgca | 540 |
| gctcttctct atgggtttat attgccactt gtcgagcttt cttacaagaa atctggtcag | 600 |
| cgaatcacgt atacgctcgc gctcgagttc cagatggtct tatgctttgc tgccacttgt | 660 |
| gtctgcctcg tggggatgct agccgctggc gatttcaagg tgatagcagg agaagcaaga | 720 |
| gattttaagc ttggagagtc tttgtactat gtggtgattg tgttcacggc cataatctgg | 780 |
| caagcatttt tgtgggagc tattgggttg atcttctgtg catcgtctct ggtctctgga | 840 |
| attatggtca gtgctctgct tccggtgacg gtgatcttgg ccgtcatttg cttccaggag | 900 |
| aagtttcagg cggggaaagg tgtcgctttg gctctctccc tctgggatc agtctcttat | 960 |
| ttctatggac aggttaaatc cgaggagaag actaaggctc aggatacaca actgtctcag | 1020 |
| cttccagtta ctgattatgt agcttaaaaa | 1049 |

<210> SEQ ID NO 3
<211> LENGTH: 1145
<212> TYPE: DNA
<213> ORGANISM: Arabidopsis thaliana

<400> SEQUENCE: 3

| ctgtttcatg tgttgatggt agaacctgaa gggaaatttt caacagaaga gagaagtcac | 60 |
| aagtactctt ggaggttaag agtgtctctc tatgtcactc tcctcttagc tggagagaca | 120 |
| atagccactc tcttaggtag actttactac gaaaaaggcg gtaaaagcac atggctcgaa | 180 |
| accttggttc agcttgtagg gtttcctttta acccttcctt gctattatta cttaaagcct | 240 |
| gagccgtcca agactaaaac cattaccaaa aaaactactt cttccttctt gacactatct | 300 |
| ttagtgtata ttggacttgg cttgcttgtt gctggacatt gtattttgta ctcatttggg | 360 |
| ctactttacc ttcctgtctc aactttctct ttgatctctg cgtcgcaatt ggcttttaac | 420 |
| gccgtcttct cttacttcct aaactcacaa aaaatcacac catttatact caattcactt | 480 |
| gttctcttaa ccatatcttc tacacttctt gttatccaac atgaaccaga atctccctct | 540 |
| tctacttcaa agtccgcagc caagtccaag tatgtgattg gatacatctg cgcggtcggt | 600 |

| agctcagctg gttattctct ggtgctttct ttaacagatt acgcgttcga aaagattcta | 660 |
| aagaaataca cattcaaggc tatttagac atggccacat atccgtctat ggtagctact | 720 |
| tgtgtagttg tggtaggact ttttggaagt ggtgggtgga aaaagctgag tacagaaatg | 780 |
| gaagagtttc aactagggaa aagctcatac attttgataa acatcggttc aacgatatca | 840 |
| tggcaagctt gtttgattgg aagtgttggt ttgattatcg aagtttcatc gcttttttcc | 900 |
| aatgtcataa gcactctttg tttaccagtt gtgcctgttc ttgctgttgt cttcttccgt | 960 |
| gatgagatga gtggaatcaa gttggttgca atgttttttgg ccatctgggg atttgtttct | 1020 |
| tatggttatc agcattatgt caatgataga aagccagaag aagaccaaga gcttcctcag | 1080 |
| tctaaagaag aagaagaaca aaaacaagta gataccattc atgtccaagc ttaggcaaag | 1140 |
| atcca | 1145 |

<210> SEQ ID NO 4
<211> LENGTH: 1293
<212> TYPE: DNA
<213> ORGANISM: Arabidopsis thaliana

<400> SEQUENCE: 4

| ggaagtcctc ttagagtggt catggaaata actcaagtaa tctatgtcaa tggtaagcaa | 60 |
| gatgcatctc gtagtgtaga ttacttgatt cttttcgcta acctgttgtt tttgatgttt | 120 |
| tcagatcata caacataga agcaaaccta acaggtcagg aggaaatgaa taccaccatg | 180 |
| gaaatcgaat cttcgtccgt acctcaatcg aagaactata agaaatggct tcgtatttcc | 240 |
| atttacgtgt tctttgtcct tgcttgccaa gcactttcta caattttggg cagagtttac | 300 |
| tatgaaaatg gtgggaagag tacatggatg ggaacacttg tccaactaat cggcttccct | 360 |
| gttctgtttc tcttccgctt ctttttcccaa accaaaaatc ccaaaccaac agaagcagat | 420 |
| ttcagaaagt tctcttcctt caccattctt ggatcagttt acatcgttac tggactatta | 480 |
| gtgtctgcta actcttatat gtcctctgtt ggtttactat acttaccagt ttctactttc | 540 |
| tccctcatct tggcctcaca attggccttc actgccttct tctcatattt tctaaactcg | 600 |
| cagaagttca ccctttcat tgtgaattct ctgtttctcc ttactatttc ctctgccctc | 660 |
| ctcgtggtca acactgattc ggaaaacaca gcaaaagtgt ctagagtaaa atatgtgata | 720 |
| gggataatat gtaccattgg tgcttctgct gggattggat tgctgctatc cctggtacaa | 780 |
| ctgatcctca ggaaggtttt aaagaagcaa acattctcaa cggtcactga cttggtcgct | 840 |
| taccaatctc tagttgcaag ctgtgtggtt ctcataggac ttttcgcaag cggggagtgg | 900 |
| aaaactttaa caagtgagat ggaaaactac aaactgggga aagtgccata cgttatgact | 960 |
| ttggcctcga tagctatttc ctggcaagtc tacaccattg gcgtcgtggg actgatcttt | 1020 |
| gagtcatctt ctgtgttctc caattccata actgctgtgg gattgcctat agttccagtt | 1080 |
| gtagcagtga ttgttttcca tgataaaatg aacgcgtcaa agatcttctc catcattta | 1140 |
| gctatctggg gattcatttc atttgtctat cagcactacc tcgacgaaaa gaagttgaag | 1200 |
| actagccaca caagtcctgt aggagatcct catctactac ctgctgagga aggtcacaca | 1260 |
| aacatacata gtgtatgatc aaaacatatt tcc | 1293 |

<210> SEQ ID NO 5
<211> LENGTH: 1194
<212> TYPE: DNA
<213> ORGANISM: Arabidopsis thaliana

<400> SEQUENCE: 5

```
tcatgagata taataaacat gagtgttaat ttttcaggtg accagaactt agaagcaaac    60
cttatagatc atgaggtggt aactgaatca tcatcatcag ctgtgcctca aaccgagaac   120
tataaaaggt ggcttcgtgt ctccatatac gtaatctttg tcctcttttg ccagccacta   180
gctacaattc tgggtagatt gtactatgaa aatggaggaa atagcacata tgtggtaaca   240
cttcttcaac tcattggctt ccctgtactg gttctgttcc gcttcttttc tcgaatcagg   300
caacccaaat caacagatac aaatttcagt cagtcccctt ccttcaccac ccttgcatcg   360
gtttacttgt gcactggact gctagtgtcc gctatgctt atttgtctgc agtagggttg    420
ctctacttac cagtctctac tttctccctc atcttggcct cacagttggc cttcactgcc   480 ttttctcat atttccttaa ctcgcaaaag ttcactcctt tgatagtcag ttctttgctt    540
ctcctcactg tatcctctgc tcttcttgtg gtcaacactg attcagaaaa ctcaactaat   600
gtatctagag tacagtatgt gatcgggttc atatgtacca tcggtgcttc cgctgggatt   660
ggactgttac tatctctgat acaaatgctc ttcaggaaag ttttcacgaa gcatacatcc   720
tcagcagtca cggacttggc catttaccag tctctagttg cgagttgtgt agttctcata   780 ggacttttg caagtggaga gtgggaaact ttgccaagtg agatgagaaa ctacaaactc    840
gggaaagtgt catatgtttt gactttagcc tcggcagcta tttcctggca agtctacact   900
cctggtcttg tgggattgat cttcgagtca tcctctgtgt tctccaattc cataacagct   960
gtgggattgc ctatagttcc agttgcggca gtgatagttt tccatgatag aatggacgca  1020
tccaaaatct tctccattat tttagctatc tgcggcttcc tttcattcgt ctatcagcac  1080
tacctcgacg aaaagaagtt gaatactagc cacacaagtg ctgtaggaga tcttcatcta  1140
cctgttgagg aaggtcacac aaacatacaa agtgtgtgat caaagcatat ttcc        1194
```

<210> SEQ ID NO 6
<211> LENGTH: 1081
<212> TYPE: DNA
<213> ORGANISM: Arabidopsis thaliana

<400> SEQUENCE: 6

```
caaatccaac agttcaagat gaaagaaatt cagtcagtag cagccaagca gaagtatctc    60
actctaacac atacaaacgg tggctcagga gtatactatg acaacggagg aaacagtaaa   120
tggctagcaa cggtagttca acttgttggc tttcctgtgc tacttccata ttatatcttg   180
tcatttaaaa cacatgcaac aactgataga gatggaaaaa gaacctcacc taggaaccgt   240
gtattggttt acgtagtgct tggacttctt gtaggagcag attgctatct gtactccatt   300
ggacttcttt acttacccgt ttctacctat tccctgatct gtgcatctca gttagccttc   360
aatgctttct tctcttatt tcttaactca caaaaactta cccctatcat tttaaattct    420
cttttcctct taactatatc ttccacccta cttgcattca ataatgagga gacagactcc   480
acaaaagtta caaaggaga gtatgtcaaa ggtttcatat gcaccgttgc tgcgtctgct    540
ggttatggtc tagtcttatc cctacaacag ctagcctttc taaaagtcct aaagaagcaa   600
aatttctcag aagttatgga tatgataatc tacgtgagtc tagtggccag ttgtgttagc   660
gtggtggggc ttttttgctag cagtgagtgg aaaactttga gcagtgaaat ggataactac   720
aaacatggga aggtatccta cattatgaac ctagtgtgga cagctgttac ctggcagtta   780
ttctccatcg gtggcacagg actgatcttg agctctcct ctctattctc aaatgcaata    840
agcgttttgg gactcccagt ggttcctatc ttggctgtaa tcatttttcca tgacaaaatg   900
```

```
aatgggttaa aggtgatttc tatgatccta gctatttggg gtttcacttc ctatgtctac    960
caacaatatc ttgatgacaa aaacttgaag aaaaatcatg aaatcacaac aacagaatcc   1020
cctgacccac cagaagcaga agagtcaact tggcaatcaa ataagctga tattttgaaa   1080
g                                                                   1081
```

<210> SEQ ID NO 7
<211> LENGTH: 1071
<212> TYPE: DNA
<213> ORGANISM: Arabidopsis thaliana

<400> SEQUENCE: 7

```
gaggggggatt ccacatctac tatgaagggg gatcaagaag tacaagtcat tggccaatca     60
gttgctacaa ttctgggcag actatactat gaaaatggag gaaacagcaa atggctagca    120
acggtagttc agcttgtagg cttttcctatt ctacttccat atcatctctt gtcagtcaaa    180
acacatacaa caactcagag agatggcaaa ttaacctcac ttaggaaccg tgcattagtt    240
tacatagtgc ttggacttct tgtaggagca gcttgctacc tatattccat tggactgctt    300
tacctacctg tttctaccct ttccctgatc tgtgcatcac agttagcctt caccgctttc    360
ttctcttatt tactcaactc acaaaaactt actcctatca ttttgaattc tcttttcctc    420
ctcactatat cttccaccct ccttgcattt aataacgagg aatcagattc caaaaaagtt    480
acaaaggag agtatgtcaa aggtttcgta tgcaccgttg gtgcatctgc tgggtttggt    540
ctactcttat ccctacaaca gctagccttt cgtaaagttt aaagaagca aactttctca    600
gaagttataa atatgataat ctacatgagt ctagtggcca gttgtgttag cgtggtgggg    660
cttttttgcta gtagcgagtg gaaaactttg agcagtgaaa tggaaaacta caaacttggg    720
aaggtatcct atgtcatgaa cctagtgtgg acagctgtta cctggcaggt attctccatc    780
ggttgcacag gactgatctt cgagcttttcc tccctattct caaatgcaat aagcgctttg    840
ggactccccg tggttcctat cctggctgtc atcattttcc atgacaaaat gaacggctta    900
aaggtgattt ctatgattct agctatttgg ggtttcgtat cctatgtcta ccaacaatat    960
cttgatgaaa caaacttgaa gaaaagtaat gaaataccaa caacagaatc ccctgaccga   1020
ccagaagcag aagggtcaag tgagcaatca aaataagctg ttacttcaaa g            1071
```

<210> SEQ ID NO 8
<211> LENGTH: 356
<212> TYPE: PRT
<213> ORGANISM: Arabidopsis thaliana

<400> SEQUENCE: 8

```
Met Lys Asn Gly Leu Ile Ile Ile Asn Cys Ile Ile Leu Thr Ile Gly
  1               5                  10                  15

Thr Cys Gly Gly Pro Leu Leu Thr Arg Leu Tyr Phe Thr Asn Gly Gly
                 20                  25                  30

Lys Arg Ile Trp Phe Met Ser Phe Leu Ser Thr Ala Gly Phe Pro Ile
             35                  40                  45

Ile Leu Ile Pro Leu Leu Val Ser Phe Leu Ser Arg Arg Arg Gly Asn
         50                  55                  60

Arg Asn Pro Asn Asn Ala Glu Asn Lys Arg Lys Thr Lys Leu Phe Leu
 65                  70                  75                  80

Met Glu Thr Pro Leu Phe Ile Ala Ser Ile Val Ile Gly Leu Leu Thr
                 85                  90                  95

Gly Leu Asp Asn Tyr Leu Tyr Ser Tyr Gly Leu Ala Tyr Leu Pro Val
```

-continued

```
                    100                 105                 110
Ser Thr Ser Ser Leu Ile Ile Gly Thr Gln Leu Ala Phe Asn Ala Leu
            115                 120                 125
Phe Ala Phe Leu Leu Val Lys Gln Lys Phe Thr Pro Phe Ser Ile Asn
        130                 135                 140
Ala Val Val Leu Leu Thr Val Gly Ile Gly Ile Leu Ala Leu His Ser
145                 150                 155                 160
Asp Gly Asp Lys Pro Ala Lys Glu Ser Lys Lys Glu Tyr Val Val Gly
                165                 170                 175
Phe Leu Met Thr Val Val Ala Ala Leu Leu Tyr Ala Phe Ile Leu Pro
            180                 185                 190
Leu Val Glu Leu Thr Tyr Lys Lys Ala Arg Gln Glu Ile Thr Phe Pro
        195                 200                 205
Leu Val Leu Glu Ile Gln Met Val Met Cys Leu Ala Ala Thr Phe Phe
    210                 215                 220
Cys Val Ile Gly Met Phe Ile Val Gly Asp Phe Lys Val Ile Ala Arg
225                 230                 235                 240
Glu Ala Arg Glu Phe Lys Ile Gly Gly Ser Val Phe Tyr Tyr Ala Leu
                245                 250                 255
Ile Val Ile Thr Gly Ile Ile Trp Gln Gly Phe Phe Leu Gly Ala Ile
            260                 265                 270
Gly Ile Val Phe Cys Ala Ser Ser Leu Ala Ser Gly Val Leu Ile Ser
        275                 280                 285
Val Leu Leu Pro Val Thr Glu Val Phe Ala Val Val Cys Phe Arg Glu
    290                 295                 300
Lys Phe Gln Ala Glu Lys Gly Val Ser Leu Leu Leu Ser Leu Trp Gly
305                 310                 315                 320
Phe Val Ser Tyr Phe Tyr Gly Glu Phe Lys Ser Gly Lys Lys Val Val
                325                 330                 335
Asp Lys Pro Gln Pro Pro Glu Thr Glu Leu Pro Ile Leu Pro Val Ser
            340                 345                 350
Asp Tyr Val Ala
        355

<210> SEQ ID NO 9
<211> LENGTH: 352
<212> TYPE: PRT
<213> ORGANISM: Arabidopsis thaliana

<400> SEQUENCE: 9

Met Val Lys Ala Leu Val Ile Ile Asn Cys Ile Ile Leu Ala Ile Gly
1               5                   10                  15
Asn Cys Gly Gly Pro Leu Ile Met Arg Leu Tyr Phe Asn Asn Gly Gly
            20                  25                  30
Lys Arg Ile Trp Phe Ser Thr Phe Leu Glu Thr Ala Gly Phe Pro Val
        35                  40                  45
Ile Phe Ile Pro Leu Leu Phe Ser Tyr Ile Thr Arg Arg Arg Ser Asn
    50                  55                  60
Asn Val Gly Asp Ser Thr Ser Phe Phe Leu Ile Lys Pro Arg Leu Leu
65                  70                  75                  80
Ile Ala Ala Val Ile Val Gly Ile Leu Ser Gly Phe Asp Asn Tyr Leu
                85                  90                  95
Tyr Ala Tyr Gly Ile Ala Tyr Leu Pro Val Ser Thr Ala Ala Leu Ile
            100                 105                 110
```

```
Ile Ala Ser Gln Leu Ala Phe Ile Ala Ile Phe Ser Phe Phe Met Val
            115                 120                 125

Lys His Lys Phe Thr Pro Phe Thr Ile Asn Ala Val Val Leu Leu Thr
        130                 135                 140

Val Gly Ala Ala Val Leu Gly Met His Thr Glu Thr Asp Lys Pro Val
145                 150                 155                 160

His Glu Thr His Lys Gln Tyr Ile Thr Gly Phe Leu Ile Thr Val Ala
                165                 170                 175

Ala Ala Val Met Tyr Ala Phe Ile Leu Pro Leu Val Glu Leu Ala Tyr
            180                 185                 190

Gln Lys Ala Lys Gln Thr Met Ser Tyr Thr Leu Val Leu Glu Phe Gln
        195                 200                 205

Leu Ile Leu Cys Leu Leu Ala Ser Ile Val Ser Val Ile Gly Met Phe
    210                 215                 220

Ile Ala Gly Asp Phe Lys Gln Ala Leu Pro Lys Glu Ala Arg Glu Phe
225                 230                 235                 240

Lys Leu Gly Glu Ala Leu Phe Tyr Val Val Ala Val Phe Ser Ala Ile
                245                 250                 255

Ile Trp Gln Gly Phe Phe Leu Gly Ala Ile Gly Leu Ile Phe Ser Thr
            260                 265                 270

Ser Ser Leu Val Ser Gly Ile Met Ile Ser Val Leu Leu Pro Ile Thr
        275                 280                 285

Glu Val Leu Ala Val Ile Phe Tyr His Glu Lys Phe Gln Ala Glu Lys
    290                 295                 300

Gly Leu Ser Leu Ala Leu Ser Leu Trp Gly Phe Val Ser Tyr Phe Tyr
305                 310                 315                 320

Gly Glu Ile Lys Ser Gly Glu Asp Lys Arg Arg Ile Gln Gln Glu Glu
                325                 330                 335

Ser Gln Glu Thr Glu Gln Ser Ser Leu Ser Arg Pro Ile Ser Glu Cys
            340                 345                 350

<210> SEQ ID NO 10
<211> LENGTH: 1067
<212> TYPE: DNA
<213> ORGANISM: Arabidopsis thaliana

<400> SEQUENCE: 10
agacaagaat ggtgaaggct cttgtgatca taaactgcat aattctagcc ataggaaact    60
gtggaggtcc tttgattatg cgtctctact tcaacaatgg cggtaaaagg atttggttct   120
ctacgtttct tgaaactgca ggctttcctg ttatcttcat tcctctgctc ttctcttaca   180
ttacccggcg cagaagcaac aatgtgggtg atagtacaag tttctttctt atcaaaccgc   240
gtcttcttat cgccgctgtt attgtaggca ttctctcagg gtttgataac tacttgtatg   300
catatggtat agcttatctt ccagtttcta cagctgctct tatcattgct tcacagttag   360
cttttatagc tatcttctca ttcttcatgg ttaacataaa gttcactcct tttaccatca   420
atgctgttgt gttgttgact gttggtgctg cggttttggg aatgcatacc gaaactgata   480
agccagttca tgagactcac aagcagtaca taactggttt cttgattact gtagcagcag   540
ctgttatgta tgctttcatc ttgccattag tggaacttgc ttaccagaaa gctaagcaaa   600
ccatgagcta tacccttgtg ctcgagttcc agttgatttt gtgtctcctt gcttctattg   660
tcagcgtcat cggtatgttc atcgctggtg atttcaagca ggccttacca aaagaagcaa   720
gagagttcaa gcttggagag gcattgttct atgtggtggc tgtgttttca gccatcatat   780
```

```
ggcaaggctt cttcttggga gccattggat taatcttctc cacatcgtct ctcgtctcgg    840
gtattatgat atcagtgctt ttgccaatta cagaggtttt agctgttata ttctaccatg    900
aaaagtttca agctgagaag ggactttctc ttgctctctc cctttggggc tttgtctctt    960
acttttatgg tgagataaag tctggcgagg ataaaaggag aattcagcag gaggagagtc   1020
aggagacaga acaatcttct ttgtcaagac ccataagtga gtgttaa                 1067

<210> SEQ ID NO 11
<211> LENGTH: 29
<212> TYPE: PRT
<213> ORGANISM: Artificial Sequence
<220> FEATURE:
<221> NAME/KEY: SITE
<222> LOCATION: (4)
<223> OTHER INFORMATION: Xaa = G, A, I, V, L, M, Y, F, W, P, S or T
<221> NAME/KEY: SITE
<222> LOCATION: (7)
<223> OTHER INFORMATION: Xaa = G, A, I, V, L, M, Y, F, W, P, S or T
<221> NAME/KEY: SITE
<222> LOCATION: (14)
<223> OTHER INFORMATION: Xaa = arbitrary amino acid residue
<221> NAME/KEY: SITE
<222> LOCATION: (18)..(20)
<223> OTHER INFORMATION: Xaa = arbitrary amino acid residue
<221> NAME/KEY: SITE
<222> LOCATION: (25)
<223> OTHER INFORMATION: Xaa = T or N
<221> NAME/KEY: SITE
<222> LOCATION: (27)
<223> OTHER INFORMATION: Xaa = I or F
<223> OTHER INFORMATION: Description of Artificial Sequence:  Motif 1

<400> SEQUENCE: 11

Leu Tyr Ala Xaa Gly Leu Xaa Tyr Leu Pro Val Ser Thr Xaa Ser Leu
 1               5                  10                  15

Ile Xaa Xaa Xaa Gln Leu Ala Phe Xaa Ala Xaa Phe Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence:  Motif 2
<221> NAME/KEY: SITE
<222> LOCATION: (3)
<223> OTHER INFORMATION: Xaa = G, A, I, V, L, M, Y, F, W, P, S or T
<221> NAME/KEY: SITE
<222> LOCATION: (9)
<223> OTHER INFORMATION: Xaa = L or E
<221> NAME/KEY: SITE
<222> LOCATION: (10)
<223> OTHER INFORMATION: Xaa = arbitrary amino acid residue
<221> NAME/KEY: SITE
<222> LOCATION: (16)
<223> OTHER INFORMATION: Xaa = G or N
<221> NAME/KEY: SITE
<222> LOCATION: (18)..(22)
<223> OTHER INFORMATION: Xaa = G, A, I, V, L, M, Y, F, W, P, S or T

<400> SEQUENCE: 12

Leu Gly Xaa Val Gly Leu Ile Phe Xaa Xaa Ser Ser Leu Phe Ser Xaa
 1               5                  10                  15

Val Xaa Xaa Xaa Xaa Xaa Leu Pro Val
            20                  25

<210> SEQ ID NO 13
<211> LENGTH: 14
<212> TYPE: PRT
```

```
<213> ORGANISM: Artificial Sequence
<220> FEATURE:
<223> OTHER INFORMATION: Description of Artificial Sequence:  Motif 3
<221> NAME/KEY: SITE
<222> LOCATION: (4)
<223> OTHER INFORMATION: Xaa = S or A
<221> NAME/KEY: SITE
<222> LOCATION: (9)
<223> OTHER INFORMATION: Xaa = G, A, I, V, L, M, Y, F, W, P, S or T
<221> NAME/KEY: SITE
<222> LOCATION: (12)
<223> OTHER INFORMATION: Xaa = G, A, I, V, L, M, Y, F, W, P, S or T
<221> NAME/KEY: SITE
<222> LOCATION: (14)
<223> OTHER INFORMATION: Xaa = Q or S

<400> SEQUENCE: 13

Leu Leu Leu Xaa Ile Trp Gly Phe Xaa Ser Tyr Xaa Tyr Xaa
 1               5                  10
```

ISOLATED NUCLEIC ACIDS CODING FOR A NUCLEAR BASE TRANSPORTER AND USES THEREOF

FIELD OF INVENTION

The present invention concerns a nucleic acid which codes for a plant or animal nuclear base transporter, and its use. In addition the present invention concerns a fragment of the nucleic acid, a construct containing the nucleic acid and/or a fragment of it, and a host cell. Included in addition in the present invention is a process for the manufacture of a transgenic cell as well as a process which influences the nuclear base transporter properties of a plant, a part of a plant and/or of seeds.

BACKGROUND OF INVENTION

Transporters play a particular role in the functioning of an organism. On the one hand they determine the uptake or emission of a substance into or out of a cell or an organism, on the other they control the transport and distribution of substances between the cells. As a rule transporters lie at the beginning or the end of a metabolic pathway and thereby take charge of fundamental higher controlling functions.

Purine and pyrimidine bases and the nucleosides and nucleotides derived from them are numbered among the transporter metabolites which serve as the building blocks of the nucleic acids. The uptake of these substances, for example during pollen fertilization and the early development of the embryo in germinating seeds, has an important physiological significance in the preparation of early stages for the synthesis of nucleic acids. As phytohormones, cytokinins are structurally closely related to the purine bases and the purine nucleosides. These phytohormones regulate many processes during plant development. Very little is known about the origin of these hormones, yet their effective transport in the plant is of decisive importance.

In bacteria nuclear base transport systems for adenine, cytosine and uracil were characterized and the corresponding genes could be cloned. In the baker's yeast *Saccharomyces cerevisiae* three differing active transport systems for nucleosides and nuclear bases have so far been well characterized both genetically and physiologically. Nucleoside transport systems have been described and characterized in a number of mammalian cells. Besides these nucleoside transporter systems specific transporter systems for nuclear bases have also been described.

In higher plants transport processes for distribution of assimilates, metabolites and phytohormones are of critical physiological importance. Only very little is yet known about the transport of nuclear bases and their derivatives in plants, and up till now in contradistinction to bacteria, fungi and mammals only a few transport systems for these substances have been described. Clarification of the course of events of nuclear base transport in plants, giving similarly detailed information as that put in place for other organisms, is not available and owing to the difficulty of molecular biological analysis in plants, is scarcely practicable. Nevertheless, there exists great interest in the identification and characterization of plant genes coding for nuclear base transporters or transporters for chemically related substances. In addition on account of the central function of transporters a great interest exists in plants, which are in a position to transport great quantities of nuclear bases and their derivatives, as well as in the provision of possibilities for altering the distribution of nuclear bases in transgenic plants and mutants.

SUMMARY OF THE INVENTION

The present invention is based on the problem of providing nucleic acids coding for plant or animal nuclear base transporters.

This problem is solved in conformity with invention through a nucleic acid, chosen from:

a) nucleic acids obtainable through complementing nuclear base transporter-deficient host cells with a plant or animal gene bank and selecting nuclear base transporter-positive host cells;

b) nucleic acids with a sequence coding for a protein with a sequence following SEQ ID NO 8 or SEQ ID NO 9;

c) nucleic acids hybridizing with a nucleic acid according to b);

d) nucleic acids which, in view of the degeneration of the genetic code, would hybridize with a nucleic acid according to b) or with the sequence complementary to b)

e) through substitution, addition, inversion and/or deletion of one or more bases, obtained derivatives of a nucleic acid according to a) to d);

f) nucleic acids complementary to a nucleic acid according to one of groups a) to e);

excluding nucleic acids with a sequence according to one of the SEQ ID NO 3 to 5.

DETAILED DESCRIPTION OF THE INVENTION

The concept "nuclear base" as used here includes not only nuclear bases and their derivatives but also substances chemically related to the nuclear bases, for example adenine, guanine and their derivatives such as xanthine, hypoxanthine, allantoin, allantoate, urate, xanthosine or inosine, cytosine and its antecedent stages and derivatives such as barbiturates or folic acid, cytokinines, such as for instance zeatine, isopentenyladenine or kinetine, and certain alkaloids, such as for instance caffeine, theobromine or nicotine. These plant-derived alkaloids show a great structural similarity to the nuclear base purine, since they likewise embody basic N-containing heterocycles. Cytokinines contain adenine as hydrophilic basic structure, on whose aminogroup in position 6 a non-polar side-chain of relatively limited specificity is situated. With kinetine what is concerned is an artificial cytokinnine which apparently does not occur naturally at all in plants. Furthermore the nuclear bases can be modified and bound to sugar or other building-blocks, e.g. adenosine as riboside of adenine, cytidine as riboside of cytosine, or cytokinine ribosides.

The term "nuclear base transporter" in the sense of the invention signifies a protein which takes part in the transport of at least one of the aforenamed metabolites through a biomembrane. This transport may happen either actively or passively. For the indication of transporter activity the method described by Ninnemann et al. (1994, *EMBO J.* 15, 3464–3471) for example may be used.

"Complementation" as used here means a compensation in the phenotype of a genetic functional defect by maintenance of the mutation on which the defect is based. Complementation in the sense of the invention is present when, for instance, a genetic defect in a gene (e.g. the FCY2 gene in

*Saccharomyces cerevisiae*) is abolished by the presence of a similar gene (e.g. the PUP1 gene from *Arabidopsis thaliana*) which takes over the function of the defective gene.

Under "nuclear base transporter-deficient host cells" in the sense of the invention one understands cells which on account of a genetic defect display negatively altered nuclear base transporter properties which lead to a negatively selectable phenotype. In carrying out the invention the preferred nuclear base transporter deficient host cells are eukaryotic cells, e.g. plant or animal cells. Nuclear base transporter deficient yeast cells are especially preferred.

Nuclear base transporter positive host cells contain a nucleic acid which leads to at least partial abolition of the genetic defect and hence manifest a positively selectable phenotype.

The identification of a nuclear base transporter may for example result through complementation of specific mutations in the yeast *Saccharomyces cerevisiae*. For isolation of a gene coding for a transporter molecule, the most closely suitable yeast mutants from a plant or animal gene bank must be available, which on account of a defect in this transporter molecule are not in a position to take up a specific substance. A mutant which is not in a position to grow in media with nuclear bases as the only source of nitrogen is for example the fcy2 mutant described by Grenson (strain MG887) (Grenson, 1969, *Eur. J. Biochem.* 11, 249–260; Polak and Grenson, 1973, *Eur. J. Biochem.* 32, 276–282). In order to be able to carry out complementation with plant or animal genes, the URA3 gene was destroyed and a uracil auxotrophe thereby produced (MG887ura3⁻).

For obtaining a nucleic acid according to the invention, a suitable yeast mutation, such as for example the fcy2/ura3 mutant, with expression plasmids suitable for use in yeast, which it carries as insertion cDNA fragments from a plant or animal cDNA library, can be transformed. Plant or animal nuclear base transporters are identified through selection of transformants which as a result of the expression of plant or animal cDNA sequences are in a position to grow on nuclear bases as the only source of nitrogen.

Surprisingly, it is now found that with expression of a cDNA library, for example from germinal tissue of *Arabidopsis thaliana*, by means of the use of suitable expression plasmids in yeast containing the phosphoglycerate kinase promoter from yeast, complementation of the fcy2 mutation is possible if the expression plasmids contain specified plant cDNA fragments. These cDNA fragments code for plant nuclear base transporters and are included in the present invention.

The expression "nucleic acids which hybridize with a nucleic acid according to b)" as used here indicates a nucleic acid which under extremely stringent conditions hybridizes with the nucleic acid according to b). For example, the hybridization with the radioactive gene specimen in a hybridization solution (25% formamide, 5×SSPE; 0.1% SDS; 5× Denhardt solution; 50 µg herring-sperm DNA; for the composition of individual components compare Sambrook et al., 1989, Molecular Cloning: a laboratory manual, $2^{nd}$ edn., Cold Spring Harbour Laboratory Press, NY, USA) can result in 20 hours at 37°. The concluding removal of non-specifically bound specimens can be carried out through multiple washing of the filter in 2×SSC/0.1% SDS at 42°. Preferably the filter is washed with 0.5×SSC/0.1% SDS, especially preferably with 0.1×SSC/0.1% SDS at 42°.

The nucleic acids according to the invention can be introduced into plasmids and by means of standard microbiological procedures undergo mutagenesis or a sequence change through recombination. In this way a particularly simple alteration in specificity of the nuclear base transporter is possible. Nucleic acids which code for changed nuclear base transporters can for example be used for the transformation of agriculturally cultivated plants with the aim of producing transgenic plants. With assistance from standard procedures (cf. Sambrook et al., 1989, Molecular cloning: a laboratory manual, $2^{nd}$ edn., Cold Spring Harbour Laboratory Press, NY, USA) base replacement can be undertaken or natural or synthetic sequences added. For the bonding of fragments to one another adaptors or "linkers" may be added to the fragments. In addition manipulations which provide appropriate cleavage sites or remove superfluous sequences or cleavage sites may be inserted. In order to undertake insertions, deletions or substitutions, such as e.g. transitions or transversions, one makes use of recognized methods such as e.g. in vitro mutagenesis, "primer repair", restriction or ligation. For analysing the nucleic acids associated with the invention ordinary methods such as e.g. sequence or restriction analysis are used, as well as further biochemical and molecular biological methods.

A nucleic acid coding for a polypeptide or protein with nuclear base transporter activity, which over its whole sequence displays at least 40%, preferably at least 60%, 80% being especially preferred, homology with a polypeptide coded by the nucleic acid according to SEQ ID NO 1 or the nucleic acid according to SEQ ID NO 10, is similarly included in the present invention.

In the context of the invention the expression "at least 40%, preferably at least 60%, 80% being especially preferred, homology" is related to agreement at the level of the amino acid sequence which can be determined according to recognized procedures, e.g. computer-supported sequence comparison (Basic local alignment research tool, S. F. Altschul et al. J. Mol. Biol. 215 (1990), 403–410).

The expression "homology", known to the specialist, signifies the degree of relationship between two or more polypeptide molecules determined through the agreement between the sequences, by which under "agreement" both identical agreement and conservative amino-acid replacement are to be understood. The percentage amount of "homology" is derived from the percentage portion of regions agreeing in two or more sequences bearing in mind gaps and other sequence peculiarities.

The expression "conservative amino-acid replacement" refers to a replacement of an amino acid residue with another amino acid residue by which the replacement does not lead to an alteration of the polarity or charge. An example of a conservative amino-acid replacement is the replacement of a non-polar amino-acid residue by another non-polar amino-acid residue. Conservative amino-acid replacements in the sense of this invention are: G=A=S, I=V=L=M, D=E, N=Q, K=R, Y=F, S=T, G=A=I=V=L=M=Y=F=W=P=S=T.

The homology of polypeptide molecules related to one another can be determined with the help of known procedures. As a rule special computer programmes have the calculation-containing algorithms for particular requirements installed. Preferred procedures for the determination of homology produce at the start the greatest agreement between the sequences investigated. Computer programs for the determination of the homology between two sequences contain but are not limited to the GCG programmes package, including GAP (Devereux, J., et al., Nucleic Acids Research 12 (12): 387 (1984); Genetics Computer Group University of Wisconsin, Madison, (WI)); BLASTP, BLASTN and FASTA (Altschul, S. et al., J. Molec. Biol. 215: 403/410 (1990)). The BLASTX program can be obtained from the National Centre for Biotechnology Information (NCBI) and from further sources (BLAST Handbook, Altschul S. et al., NCB NLM NIH Bethesda Md. 20894; Altschul, S., et al., J. Mol. 215:403–410 (1990)). The well-known Smith Waterman algorithm may also be used for the determination of homology.

Preferred parameters for the comparison of sequences include those below:
Algorithm: Needleman and Wunsch, J. Mol. Biol. 48: 443–453 (1970)
Comparison matrix: BLOSUM 62 by Henikoff and Henikhoff, Proc. Natl. Acad. Sci. USA 89:10915–10919 (1992)
Gap penalty: 12
Gap length penalty: 4
Threshold penalty of similarity 0

The GAP programme is also suitable for use with the above parameters. The above parameters are the standard parameters (default parameters) for amino-acid sequence comparisons.

Further specimen algorithms, gap opening penalties, gap extension penalties, comparison matrices including the Wisconsin package version 9, September 1997, mentioned in the programme handbook, may be used. The choice depends on the comparison being carried out and furthermore on whether the comparison is being carried out between pairs of sequences, for which GAP or Best Fit are preferred, or between a sequence and a comprehensive sequence data bank, for which FASTA or BLAST are preferred.

A nucleic acid which codes for a polypeptide or protein with nuclear base transporter activity, which over a section of at least 20 amino-acids displays at least 60%, preferably at least 75%, 90% being especially preferred, homology with one of the polypeptides coded for by the nucleic acids according to SEQ ID NO 1 and the nucleic acids according to SEQ ID NO 10, is similarly included in the invention. Preferably the nucleic acid sequence according to the invention codes for a polypeptide or protein with nuclear base transporter activity which includes a nucleic acid sequence which displays at least 70%, preferably at least 80%, 90% being especially preferred, homology with one of the following amino-acid sequences:

(a) L Y A X G L X Y L P V S T X S L I X X X Q L A F X A X F S (SEQ ID NO 11) in which X in positions 4 and 7 stands for a hydrophobic amino-acid (G, A, I, V, L, M, Y, F, W, P, S, or T), in positions 14 and 18–20 for an optional amino-acid, at position 25 for T or N and at position 27 for I or F;

(b) L G X V G L I F X X S S L F S X V X X X X X L P V (SEQ ID NO 12) in which X at positions 3 and 18–22 stands for a hydrophobic amino-acid (G, A, I, V, L, M, Y, F, W, P, S or T), at position 10 for an optional amino-acid, at position 9 for L or E and at position 16 for G or N;

(c) L L L X I W G F X S Y X Y X (SEQ ID NO 13) in which X in positions 9 and 12 stands for a hydrophobic amino-acid (G, A, I, V, L, M, Y, F, W, P, S or T) in position 4 for S or A and in position 14 for Q or S.

The nucleic acids preferably contain the coding sequence for one of the sequences according to the SEQ ID NO 1, 2, 6, 7, or 10, or one of these through substitution, addition, inversion and/or deletion of one or more bases obtained derivatives. In a particularly preferred model of the invention the nucleic acid is a DNA.

The subject of the invention is similarly a fragment of the nucleic acid according to the invention, which in anti-sense orientation to a promoter can limit the expression of a nuclear base transporter in a host cell. This fragment can contain at least 10, preferably at least 50, very particularly preferably at least 200 nucleotides. This fragment can be introduced into a host cell and there transcribed into a non-translatable RNA (anti-sense RNA) which through bonding to an endogenous nuclear base transporter gene or to the mRNA transcribed therefrom can inhibit their expression.

The invention further concerns a construct which contains a nucleic acid according to the invention and/or a fragment according to the invention, itself under the control of the expression-regulating elements. Examples of such regulating elements are constitutive or inducible promoters, such as for bacteria the E. coli promoter araBAD (Carra & Schlief, 1993, EMBO J. 12, 36–44), for fungi the yeast promoter PMA 1 (Rentsch et al., 1995, FEBS Lett. 370, 264–268) and for plants the viral promoter CaMV35S (Pietrzak et al, Nucl. Acids Res. 14, 5857–5868). In addition the nucleic acids or the fragment can be provided with a transcription termination signal. Elements of that kind have already been described (see e.g. Gielen et al, 1984, EM80 J. 8, 23–29). The transcription initiating region may be either native (homologous) or foreign (heterologous) to the host organism. The sequence of the transcription initiating and termination regions may be artificially manufactured or naturally acquired or contain a mixture of synthetic and natural components. Preferably the nucleic acid or the fragment in the construct are found in anti-sense orientation to the regulator element. The construct can for example be introduced into the plant genome and after its transcription lead to suppression of the formation of nuclear base transporter molecules suitable for plants. In an especially preferred embodiment of the invention the construct is present in a plasmid.

The plasmid can contain a replication signal for E. coli or yeast and a marker gene, permitting positive selection of host cells transformed with the plasmid. If the plasmid is introduced into a plant host cell, further sequences known to the expert may be required, each depending on its mode of introduction. If the plasmid according to the invention is for example a derivative of the Ti or Ri plasmid, the introducing nucleic acid or the introducing fragment must be flanked by T-DNA sequences which facilitate integration of the nucleic acid or the fragment into the plant genome. The use of T-DNA for the transformation of plant cells has been intensively investigated and is described among others in EP 120 516, Hoekema, The Binary Plant Vector System, Offsetprinter Kanters B. V. Ablasserdam (1985), chapter 5, Fraley et al Crit. Rev. Plant Sci. 4, 1–46 and An et al., 1985, EMBO J. 4, 277–287. Once the introduced nucleic acid or fragment is integrated into the genome, it is as a rule stable therein and is contained also in the progeny of the original transformed cell. The integrated sequence may similarly contain a selection marker which confers resistance to a biocide or an antibiotic such as kanamycin, G418, bleomycin, hygromycin or phosphinotricin on the transformed cell. The marker individually used should thereby distinguish cells transformed by selection from cells in which the introduced DNA is lacking.

The subject of the invention is in addition a host cell containing a nucleic acid according to the invention and/or a nucleic acid with a sequence according to one of the SEQ ID NO 3 to 5 and/or a fragment of the aforenamed nucleic acid and/or a construct according to the invention. The host cell in conformity with the present invention may be chosen from bacteria, yeast, mammalian and plant cells.

In addition the present invention concerns a transgenic plant as well as plant cells and/or seeds of this plant, containing a nucleic acid according to the invention or a nucleic acid with a sequence according to one of the SEQ ID NO 3 to 5 and/or a fragment of the abovenamed nucleic acids and/or a construct according to the invention. Preferably the nucleic acid, the fragment and/or the construct integrates into a site on the genome which does not correspond to its natural position.

The present invention similarly concerns a protein which through expression of a nucleic acid according to the invention or a nucleic acid with a sequence according to one of the SEQ ID NO 3 to 5 is obtainable in a host cell. The relevant initiation codons (ATG) of nos. 1 to 7 have been identified in the sequence listing underlining. Preferably the protein possesses the same nuclear base transporting properties as those of the protein having SEQ ID NO 8 or the SEQ ID NO 9. As indication of the activity of such a protein uptake experiments may be carried out, as described in the examples. Antibodies which react with a protein according to the invention are similarly included in the invention.

A further object of the invention is the provision of a procedure for the production of a transgenic plant. This object is accomplished through a procedure consisting of the following steps:

Introduction of a nucleic acid according to the invention or a nucleic acid with a sequence according to one of the SEQ ID NO 3 to 5 and/or a fragment, conforming to the invention, of the aforementioned nucleic acid, into a plant cell; and Regeneration of a plant from the transformed plant cell.

Transgenic plants which are produced in accordance with the invention procedure may be derived from e.g. tobacco, potato, sugar-beet, soya-bean, coffee, pea, bean, cotton, rice or maize plants.

For the introduction of the nucleic acid or the fragment into a plant cell there are besides transformation with the help of *agrobacteria* still numerous further techniques available. These techniques include the fusion of protoplasts, the microinjection of DNA, electroporation such as projectile methods and virus infection. From the transformed plant cells entire plants can then be regenerated in a suitable medium, which may contain antibiotics or biocides for selection. Plants obtained in this way can then be tested for the presence of the introduced DNA.

Unlike in transformation with the assistance of *agrobacteria* no special demands are made on the vector by injection and electroporation. Simple plasmids such as pUC derivatives can be used. Should whole plants be regenerated from cells transformed by such means, however, the presence of a selectable marker gene is advantageous. The transformed cells grow inside the plants in the usual way (see also McCormick et al., 1986, *Plant Cell Reports* 5, 81–84). These plants can as usual be raised and crossed with plants possessing the same transformed or other genetic background. The hybrid individuals resulting therefrom have the corresponding phenotypic properties.

The subject of the present invention is similarly a procedure for influencing the nuclear base transporter properties of a plant, part of a plant, a plant cell, and/or of seeds, which contains the following step:

Introduction of a nucleic acid in conformity with the invention or a nucleic acid with a sequence according to one of the SEQ ID NO 3 to 5 and/or a fragment, in conformity with the invention, of the aforementioned nucleic acid, into a plant cell or a plant.

For influencing the nuclear base transporter properties of a plant, both alterations in the specificity of the transport system which facilitate the transport of new combinations, and those which evoke a change in the transport mechanism, are appropriate. For example alterations are possible which change the affinity or substrate specificity of the transporters resulting in a more efficient nuclear base transport in the leaves or changes in apical dominance, the process of blooming or senescence, or make possible an improved dispersion of pesticides.

The plant cells in accordance with the invention can be used for the regeneration and production of entire plants. The nucleic acids in accordance with the invention as well as nucleic acids with a sequence according to one of the SEQ ID NO 3 to 5 can be used for isolating homologous sequences from bacteria, fungi, plants, animals and/or people. To be able to search for homologous sequences, gene banks must first be established which are representative of the gene profile of an organism or of the expression of genes in this organism. Firstly there are genomic, lastly there are cDNA banks. From these related sequences can be isolated with the help of a probe among the aforementioned nucleic acids. Once one has identified and isolated the gene belonging to it, determination of the sequence and an analysis of the properties of the proteins coded by this sequence is possible.

A further use of the aforementioned nucleic acids concerns the expression of a nuclear base transporter in prokaryotic and eukaryotic cells. If the aforementioned nucleic acids are introduced into a prokaryotic cell an RNA sequence of a eukaryotic nuclear base transporter translatable by bacteria is constructed, which despite the considerable differences in the membrane structure of prokaryotes and eucaryotes is translated into a functional eukaryotic nuclear base transporter with its substrate specificity. This makes possible the use of bacterial lines for studies of the transporter as well as its substrate. The aforementioned nucleic acids can similarly be used under the control of a regulatory element in antisense orientation for the inhibition of the expression of an endogenous nuclear base transporter in prokaryotic and/or eukaryotic cells. The manufacture of transgenic useful plants represents a further possibility for the use of these nucleic acids.

Further uses are:

If the transporter is essential for the function of the plant, it can serve as a herbicide target: screening procedures in yeast in order to search for inhibitors, these can be optimized in the yeast system and through chemical modification and then tested on the plants.

Since substitution in the basic structure of the substrate is allowed, one can use the transporter to mobilize pesticides, e.g. through affixing purine and pyrimidine residues to fungicide or insecticide.

Special uses are:

1. Substrate class A: Transporters are responsible for the transport of secondary metabolites or alkaloids such as caffeine, theobromine, nicotine and similar substances.

Over-expression or ectopic expression under the control of various promoters such as CaMV-35S or specific promoters in order the better to transport secondary metabolites of these substance classes in particular organs, e.g. leaves at harvest-time, seeds and tubers or beetroots.

Cosuppression or antisense repression in order to diminish the content of secondary metabolites of that type, especially toxic substances in particular organs, egg the products of nutrition; egg as a new type of decaffeinating agent.

Secondary metabolites are important defensive substances of plants against infections and animal consumption. Improved care of the organs affected can lead to improved resistance and ability to fight back.

Secondary metabolites as pharmaceutical products (plant as bioreactor). An optimal care of crop organs is essential for the extractability and can be attained by optimized transport in transgenic plants.

2. Substrate class B: Transporters are responsible for the transport of nuclear bases and derivatives, e.g. on the one hand adenine, xanthine, allantoin, hypoxanthine, urate, xanthosine, inosine; on the other hand cytosine and its derivatives such as barbiturate and folic acid, but also nucleosides such as adenosine, etc. Reversal of transport processes in transgenic plants leads to altered cell division activity and improved development of autonomous cells: nuclear bases play an important role in DNA and RNA synthesis and thereby in cell division activity, for example pollen is supplied with nuclear bases. Useful for the creation of sterile male pollen through transport inhibition.

in the transport of allantoic acid a role in the fixation of atmospheric nitrogen. Intercellular transport is important for the nitrogen assimilation of plants.

Adenine is an essential building-block for ATP. The external supply e.g. of the phloem with ATP could, through alteration of expression, be influenced positively or negatively in transgenic plants by PuP transporters.

3. Substrate class C: Transporters are responsible for the transport of plant hormones, e.g. cytokinins and cytokinin derivatives, e.g. ribosides (see adenine/adenosine).

Since cytokinins play a central role in the control of development and metabolic processes, an alteration in activity can, due to Over-expression, ectopic expression or repression (through cosuppression or anti-sense) in transgenic plants lead to improved endurance (control of sink-source relationships), changed degree of branching (role in apical dominance), improvement in the germination situation of seeds, delay or prolongation of bud formation and delay or prolongation of senescence (cytokinins prolong senescence). In addition the cell division activity is influenced, and thereby the formation of side-roots, the size and capacity of the organs of production, morphogenesis in tissue culture, the expansion of the leaves and the regulation of water efficiency on account of the influence on stoma opening and the development of plastids.

4. Transport of related substances: Auxines are also structurally close to the spectrum of the substrates transported by the nuclear base transporters and could be similarly modified by the transporters. The entire spectrum of auxine operations can be influenced by an alteration in the transport of auxines.

5. Modification of the transport characteristics of transporters by mutagenesis. Broadening the substrate spectrum, e.g. in the direction of the transport of alkaloids, which have hitherto not been recognized by the transporters, synthetic hormones, which are poorly transported, nuclear bases which are not transported efficiently enough, as a springboard for the alteration of transport processes in transgenic plants.

Up till now homologues of almost all new plant transporters could be found in animal or human genomes (examples: glucose transporters of the plant family MST are related to the animal GLUT transporters at a sequence level, amino-acid transporters of the AAP family were later found in animals (VGAT, SN1); amino-acid transporters of the CAT family in animals and plants are related). On the basis of resemblance of biochemical properties, which were discovered for the animal/human transport of adenine and the competition by caffeine, it is postulated that a hitherto unidentified homologue of PUP is responsible for the nuclear base/nucleoside and derivative transport in these systems. The expression of this system in yeast cells as an evidence of function enables first the description, then the identification of possible plant diseases provoked by defects in the systems, the identification of new structures leading to pharmaceuticals and the influencing of the transport of substances across the blood-brain barrier, since the adenine/caffeine transport occurs at this site.

BRIEF DESCRIPTION OF THE DRAWINGS

The following figures illustrate the invention.

FIG. 5 shows represented in the form of a diagram the results of an uptake experiment in which the cytokinin uptake of the yeast line MG877ura3⁻::PUP1 was investigated by means of $^3$H-labelled zeatine. The uptake was set temporarily at a concentration of 100 μM trans-zeatin. In this case PUP1 was expressed under control of the yeast ATPase promoter PMA1 in the vector pDR195 (Rentsch et al., 1995, *FEBS Left.* 370, 264–368) in the mutant MG877ura3⁻::(FCY). The empty vector (FCY2pDR195) served as control.

EXAMPLES

Figure 1:
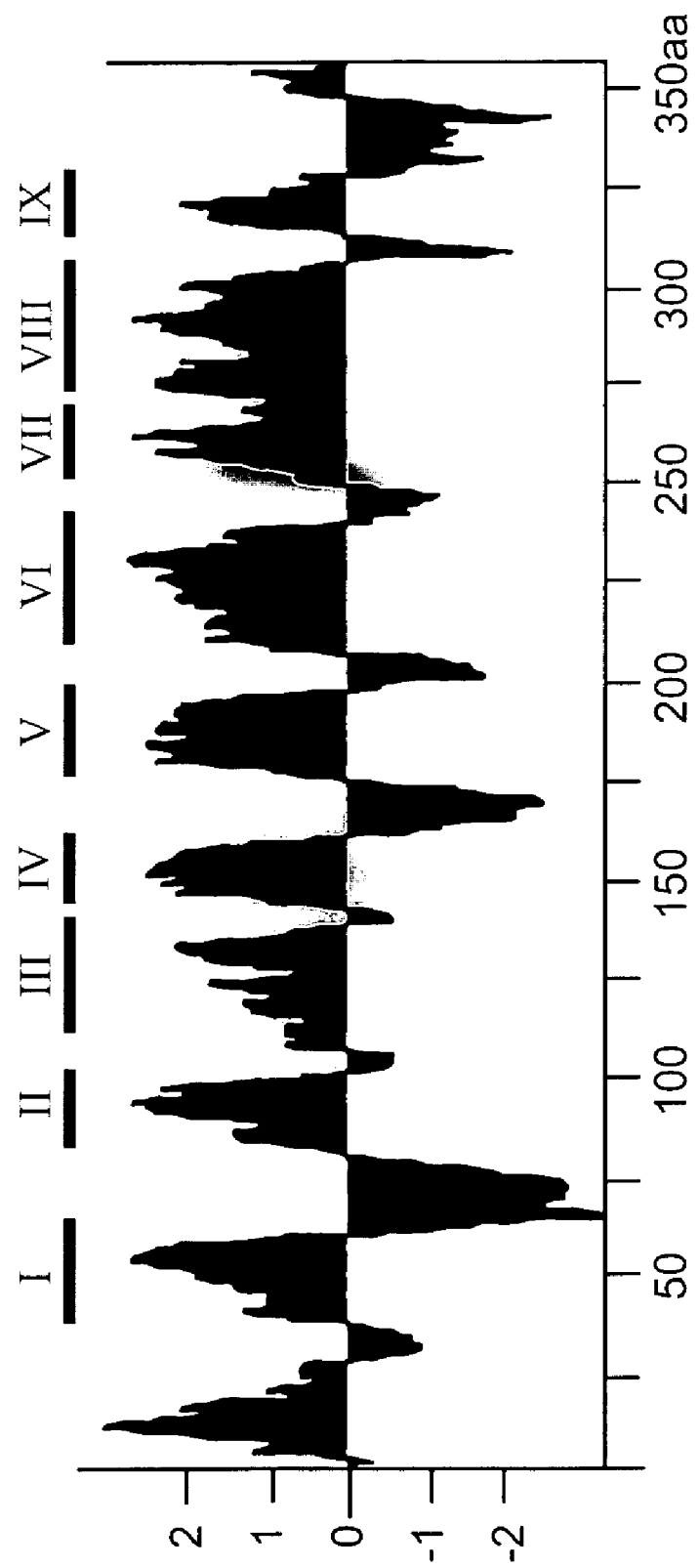
FIG. 1 shows a hydrophobicity analysis of the PUP nuclear base transporter protein after Kyte and Doolittle.

General Methods a) Cloning procedure: For cloning in *E. coli* the vector pT7T3 18U (Pharmacia) and for transformation of yeasts the vector pFL61 (Minet & Lacroute, 1990, *Curr. Genet.* 18, 287–291) were inserted. For plant transformation the gene constructions in the binary vector pBinAR, a derivative of pBIN19 (Bevan. 1984, *Nucl. Acids Res*, 12, :8711–8721) were cloned.

b) Bacterial and yeast strains: For the pT7T3 18U- and pFL61 vectors as well as for the pBinAR constructs the *E. coli* strain DH5α was used. As initiating strain for the expression of the cDNA library in yeast the yeast strain MG887 (Dubois & Grenson, 1979, *Mol. Gen. Genet*, 175, 67–76) with the mutation fcy2 was used, after a ura3 deficiency had been induced.

c) Transformation of *Agrobacterium tumefaciens*: DNA transfer in the *Agrobacteria* resulted through direct transformation by the method of Höfgren and Willmitzer (1988, *Nucl. Acids Res*. 16, 9877). The plasmid-DNA-transformed *Agrobacteria* were isolated by the method of Bimboim and Doly (1979, *Nucl. Acids Res*. 7, 1513–1523) and electrophoretically analysed following suitable restriction division.

d) Transformation of plants: The plant transfers can result from *Agrobacterium tumefaciens*-mediated (strain C58CI, pGV2260) gene transfer (Deblaere et al., 1985, *Nucl. Acids Res*. 13, 4777–4788). The transformation of *A. thaliana* is for example carried out by means of vacuum infiltration (modified after Bechtold et al. (1993) Comptes Rendus de l'Academic des Sciences Serie III, Sciences de la Vie 316: 1194–1199). Pots (diameter 10 cm) are filled with earth and finally covered with a fly-net. On this net *A. thaliana* seeds are sown. Six to eight weeks after the sowing the plants are used for vacuum infiltration. For vacuum infiltration some of the corresponding *Agrobacterium* strains are cultivated as 2×1 liter cultures in YEB+antibiotic (50 μg/ml kanamycin and 100 μg/ml rifampicin) at 28° C. At OD₆₀₀ the cells from 3000 g are harvested and resuspended in 600 ml infiltration medium (0.5×MS medium (Sigma), 5% sucrose, 44 μM benzy-laminopurine. The bacterial suspension is filled into 250 ml Weck tubes and placed in an exsiccator. The *A. thaliana* plants are immersed "head-up" in the bacterial suspension and then for 5 minutes vacuum is applied. After 3–4 weeks the seeds of these plants are harvested. For surface sterilization the seeds are shaken for 10 minutes in 4% sodium hypochlorite, 0.02% Triton, centrifuged out at 1500 g, washed four times in sterile water and resuspended in 3 ml 0.05% agarose per 5000 seeds. The seed-agarose solution is spread out on MSS medium (1×MS, 1% sucrose, 0.8% agarose, 50 μg/ml kanamycin, pH 5.8) (plates of 13.5 cm diameter for 5000 seeds). To reduce the loss of moisture the plates are closed off with Parafilm®. The kanamycin-resistant plants are transferred to earth. Seeds from these plants are harvested and analysed.

e) Demonstration of nuclear base transporter activity: Demonstration of the activity can be carried out for example through uptake experiments with radioactive substrates (e.g. [¹⁴C] adenine) in the fcy2 yeast mutants (MG871 ura3⁻::pFL61-PUP1) transformed with the plant transporter gene under the control of the yeast promoter, in principle as described in Ninnemann et al., 1994 (*EMBO J*. 15, 3464–3471). Alternatively other expression systems may be introduced, e.g. *Xenopus* oocytes (Boorer et al.; 1996, *J. Bioi. Chem*. 271, 2213–2220), with the employment of electrophysiological measurement methods.

Example 1

Cloning of the PUP1 Nuclear Base Transporter Gene from *Arabidopsis thaliana*

The cloning of the PUP1 nuclear base transporter was accomplished by complementation of the yeast strain MG887ura3⁻ (fyc2) (this work; preliminary step MG887 Grenson 1969, *Eur. J. Biochem*. 11, 249–260) with a cDNA gene bank from *Arabidopsis thaliana* and the selection of nuclear base transporter positive cells. The fyc2 yeast mutant cannot grow in media with adenine or cytosine as the only source of nitrogen (Grenson, 1969, *Eur. J. Biochem*. 11, 249–260; Polak. & Grenson, 1973, *Eur. J. Biochem*. 32, 276–282). For the introduction of an auxotrophy marker (ura3⁻) the nuclear uptake-deficient mutant MG887 (Dubois & Grenson, 1979, *Mol. Gen. Genet*. 175, 67–76) was transformed with a fragment of the URA3 gene, which carries an internal deletion. Through selection at the toxic preliminary step 5-fluoro-orotate a URA-deficient mutant MG887ura3⁻ could be isolated For complementation of the nuclear base transport mutation of the yeast strain MG887ura3⁻ cloned cDNA from young embryos of *Arabidopsis thaliana* (at the two-leaf stage) are used (Minet et al., 1992, *Plant J*. 2, 417–722). About 1 μg of the vector with a cDNA insertion was transformed in the yeast strain MG887ura3⁻ according to the method of Dohmen et al. (1991, *Yeast* 7, 691–692). Yeast transformants which could grow in minimal medium with 1 mM adenine as the only source of nitrogen were propagated. From these clones plasmid DNA was isolated by standard means. The strain MG887ura3⁻ was once more transformed with the plasmid isolated. In this way a plasmid pFL61-PUP1 which can complement the fcy2 mutation was obtained. This plasmid has an insertion of 1.2 kilobases containing the PUP1 nuclear base transporter gene.

The yeast strain MG887ura3⁻::pFL61-PUP1 obtained by transformation of MG887ura3⁻ with the plasmid pFL61-PUP1 is used for uptake studies with adenine or nuclear bases. Through gene engineering alteration of the coding region of the nuclear base transporter gene PUP1 according to standard procedures (cf. Sambrook et al., Molecular cloning: a laboratory manual, $2^{nd}$ edn., Cold Spring Harbor Laboratory. Press, NY, USA) its specificity or the characteristics of the transport mechanism may be changed. The strain MG887ura3⁻::pFL61-PUP1 is directly suitable for the investigation of inhibitors or promoters of nuclear base transport.

The PUP1 protein expressed by the yeast strain MG887ura3⁻::pFL61-PUP1 was subjected to hydrophobocity analysis by the method of Kyte and Doolittle. As can be seen from FIG. 1, the PUP1 protein displays 9–12 strongly hydrophobic regions (positive values on the Y axis) which are long enough in each instance to stretch once across the membrane. The first hydrophobic region is not conserved in all PUP proteins.

Sequence Analysis of the cDNA Insertion of the PFL61-PUP1 Plasmid

The plasmid pFL61-PUP was isolated from the yeast strain MG887ura3⁻::pFL61-PUP1 and with the aid of synthetic oligonucleotides the insertion was sequenced by the method of Sanger et al. (1977, *Proc. Natl. Acad. Sci USA* 74, 5463–5467). The coding sequence of the PUP1 gene is reproduced in SEQ ID NO 1 and that of the protein sequence derived from it in SEQ ID NO 8.

Example 2

Uptake Studies on the Yeast Strain MG887ura3⁻pFL61-PUP1 with $^{14}$C-Labelled Cytosine and $^3$H-Labelled Cytokinins For measuring the rate of uptake the yeast strains MG887ura3⁻::pFL61, MG887ura3⁻::pFL61-PUP1 and their original strain Σ1278b (Dubois & Grenson, 1979, *Mol. Gen. Genet.* 175, 67–76) were cultured in complete medium (YPD) without uracil and with 2% glucose as carbon source up to an $OD_{600}$ of 0.6 at 28° C. The cells were harvested at 3000 g, washed twice with water and brought to an $OD_{600}$ of 12 with sodium phosphate buffer (100 mM, pH 4.5), 1% glucose. The cell suspension was stored in 100 μl portions on ice up to the beginning of the uptake measurements. Before the start of the uptake measurements the cells were pre-incubated at 30° C. for 2 minutes. The reaction was then started, by which 100 μl of radioactively labelled substrate solution was added to 100 μl cell suspension. The reaction mixture was incubated at 30° C. and after 30, 60, 120 and 180 seconds in each case 50 μl of suspension was withdrawn and placed in 4 ml of ice-cold water (in measurements over 180 seconds more cell suspension and substrate solution were correspondingly added). The cells were absorbed on to glass fibre filters and washed with 4 ml of ice-cold water. The radioactivity on the filters was finally ascertained in a liquid scintillation counter.

Substrate solution: For the substrate solution what is concerned is a 100 mM sodium phosphate buffer pH 4.5 with 1% glucose and 9.25 Bq/μl of radioactively labelled substrate (25–100 μM [$^{14}$C] adenine or [$^{14}$C] cytosine). In addition the substrate solution contains the unlabelled substrate, possible inhibitors and competitors in double end-concentration. For estimation of the optimum pH the pH value of the sodium phosphate buffer is also changed. When the influence of glucose on the uptake rate is measured neither the cell suspension nor the substrate solution contains glucose. Glucose is only added after starting the uptake measurements at the commencement of measuring at an end-concentration of 1%. Furthermore it could be shown that PUP2 was also in a position to transport adenine.

In Table 1 the uptake of radioactively labelled adenine and cytosine mediated by the PUP1 nuclear base transporter is indicated by the yeast strain MG887ura3⁻::pFL61-PUP1. For calculation of the intracellular concentration the cell volume is estimated as four times the dry weight (Ninnemann et al., 1994, *EMBO J.* 15, 3464–3471). The uptake occurs against a concentration gradient.

TABLE 1

|  | Initial concentration Medium | End conc. Medium | End conc Cells | Enrichment factor |
| --- | --- | --- | --- | --- |
| Adenine | 200 μM | 155 μM | 2350 μM | 15 |
| Cytosine | 200 μM | 145 μM | 2660 μM | 18 |

The influence of various inhibitors on the adenine or cytosine uptake mediated by the PUP1 nuclear base transporter in the yeast strain MG887ura3⁻::pFL61-PUP1 is indicated in Table 2. The inhibitors were added to the cells five minutes before beginning the measurements. The protonophores carbonyl-cyanide-m-chlorphenylhydrazone (CCCP) and 2,4-dinitrophenol (2,4-DNP) and the $H^+$/ATPase inhibitor diethylstilborestrol block the uptake. This may be taken as a clear indication of a secondarily active proton-associated uptake mechanism.

TABLE 2

| Inhibitor | Relative adenine uptake [%] | Relative cytosine uptake [%] |
| --- | --- | --- |
| without inhibitor | 100 | 100 |
| 100 μM diethylstilboestrol | 4 | 8 |
| 100 μM DCCD | 47 | 55 |
| 100 μM CCCP | 13 | 20 |
| 100 μM 2,4-DNP | 54 | 58 |
| 10 μg/ml cycloheximide | 95 | 97 |

Figure 2:
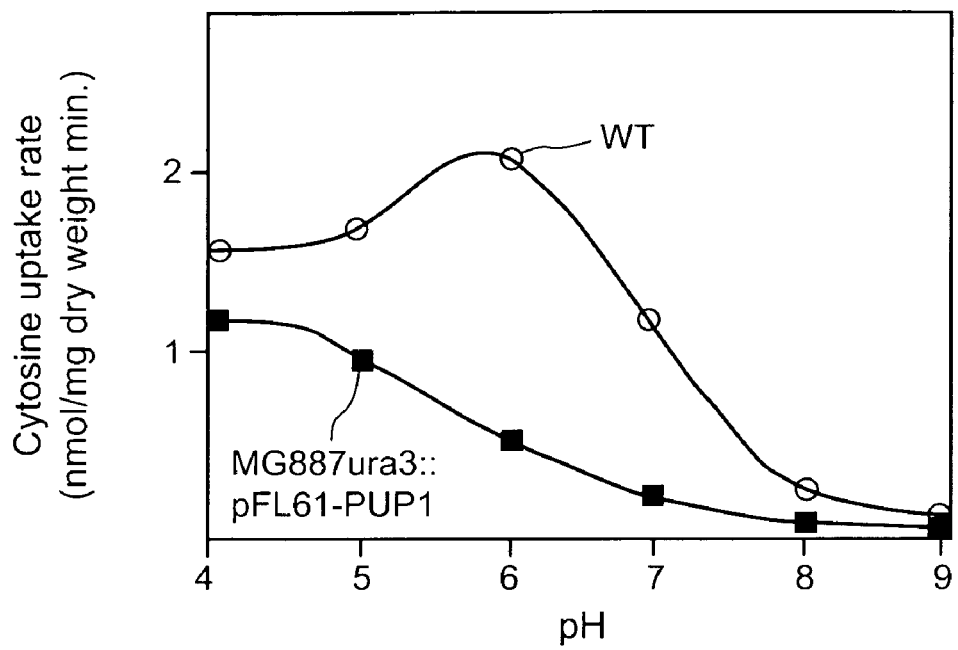
FIG. 2 shows represented in the form of a diagram the results of an uptake experiment, in which the cytosine uptake rate of the yeast line MG877ura3⁻::pFL61-PUP1 and of the wild-type line Σ1278b (Dubois & Grenson, 1979, *Mol. Gen. Gener.*, 175, 67–76) were measured at various pH levels. The substrate concentration amounted to 100 μM.
Figure 3:
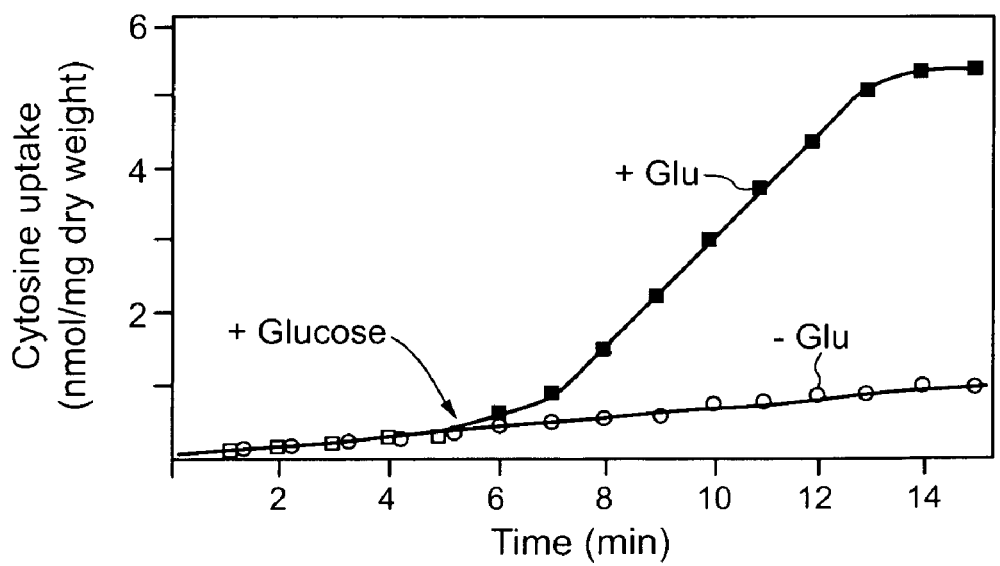
FIG. 3 shows represented in the form of a diagram the results of an uptake experiment in which the cytosine uptake of the yeast line MG877ura3⁻::pFL61-PUP1 was measured with and without the addition of glucose. The cells were washed twice with water and incubated at room temperature for 30 minutes before measurement of the uptake began. Five minutes after the measurements began a test supplementation of glucose to a final concentration of 1% was added.

FIG. 2 shows that the cytosine uptake into the yeast strain MG887ura3⁻::pFL61-PUP1 mediated by the PUP1 nuclear base transporter is dependent on the pH level. Similar results were attained for the adenine uptake (data not shown). As shown in FIG. 3, the cytosine uptake into the yeast strain MG887ura3⁻::pFL61-PUP1 mediated by the PUP1 nuclear base transporter is glucose-dependent. Similar results were obtained for the adenine uptake (data not shown). The increase of activity on the addition of glucose may be taken as an indication of energy dependence. This as well as the observed increase of activity with a decline in the pH level points towards a secondarily active proton-associated uptake mechanism.

Figure 4:
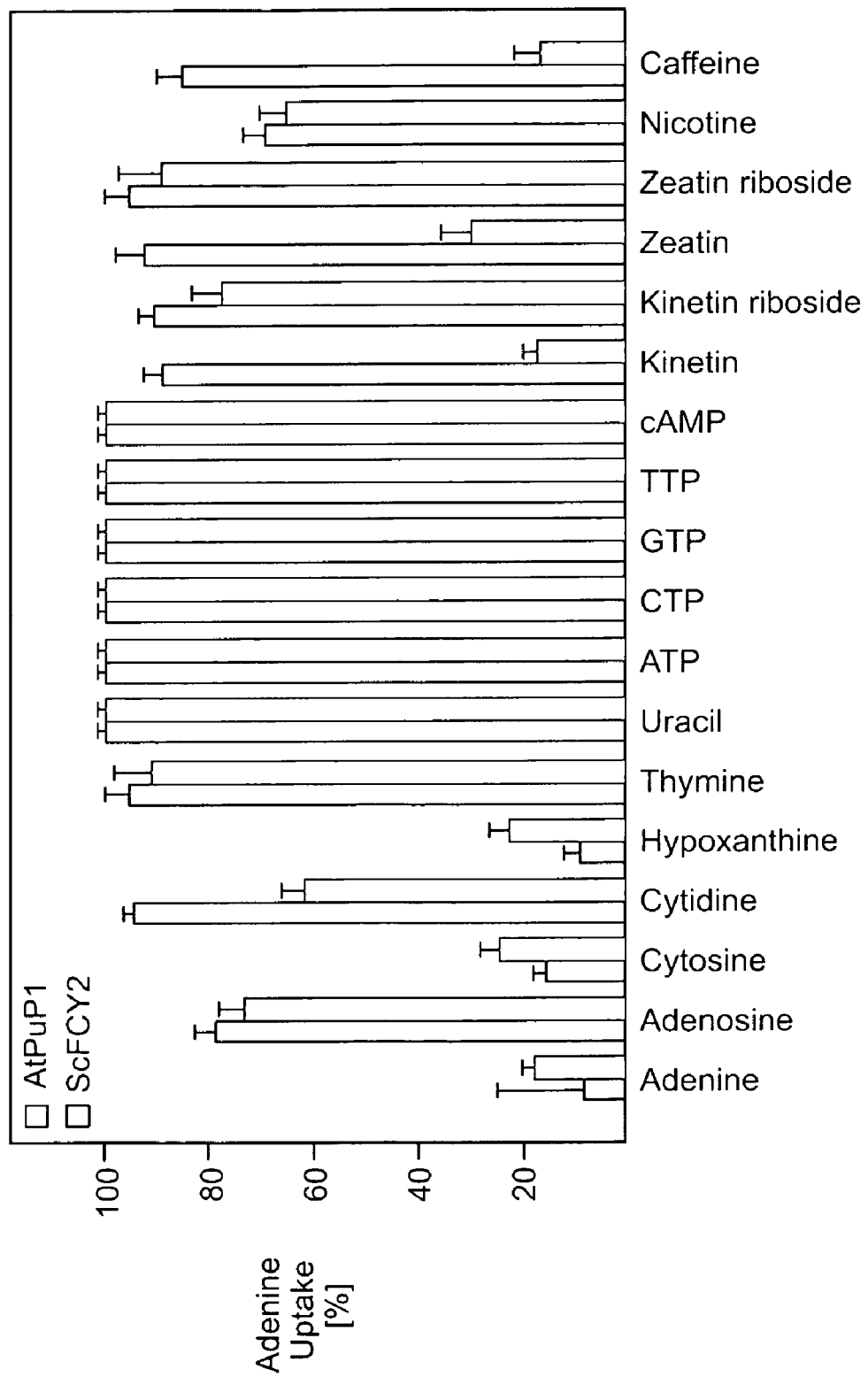
FIG. 4 shows an analysis of the substrate specificity of the PUP1 nuclear base transporter expressed in the yeast (black bar) compared to the yeast's own FCY-2 transporter (white bar).

For investigating the substrate specificity of the PUP1 nuclear base transporter expressed in yeast in comparison to the yeast's own FCY2 transporter, competition experiments with non-radioactive substrates were carried out. The results of these experiments are shown in FIG. 4. The uptake of radioactively labelled adenine was measured set at 100% (corresponding to 1.7 or 0.9 nmol.min$^{-1}$.mg$^{-1}$ dry weight). The measurements were carried out at a substrate concentration of 25 μM. The competitors were added in 10 times molar excess.

For the analysis of competitive inhibition by the cytokinins kinetin and zeatin of adenine transport mediated by the PUP1 nuclear base transporter uptake investigations were carried out with different concentrations of radioactively labelled adenine as well as various competitor concentrations. From Lineweaver/Burk calculations the inhibitor constants Ki were determined (35 µM for kinetin and 30 µM for zeatin).

Direct uptake experiments in PUP1-expressing yeast cells with $^3$H-labelled cytokinins (zeatine and 2-isopentenyl adenine) show that PUP1 can also transport cytokinins (FIG. 5). The uptake experiments were carried out with $^3$H-labelled zeatine in MG887ura3$^-$ as for adenine. To start the reaction 87.3Bq/µl of the radioactive substrate was added to a total concentration of 100 µM trans-zeatine. The results of three independent experiments showed a 70 times increased uptake of radioactively labelled trans-zeatine for the PUP1-expressing yeast clone as against the control strain transformed with the control plasmid pDR195. This shows that PUP1 mediates the transport of trans-zeatine.

Example 3

Transformation of Plants with Constructions for Over-Expression or Antisense Repression of a Nuclear Base Transporter Gene The introduction of a nucleic acid coding for a plant nuclear base transporter and the over-expression or the antisense repression of a nuclear base transporter gene for the alteration of the transport of nuclear bases and their derivatives is described here with *Arabidopsis thaliana* as example. Its use is nevertheless not confined to this species.
a) Over-expression: The 1.2 kb NotI fragment from the plasmid pFLP-PUP1, which contains as an insertion the cDNA for a nuclear base transporter of *Arabidopsis thaliana*, was cloned in the vector pT7T3 18U/NotI excised with NotI. The vector pT7T3 18UINotI was created because in the SmaI excision site of pT7T3 18U a NotI linker was included. The orientation of the fragment was checked by restriction splitting. The vector includes a KpnI and an XbaI excision site in the multiple cloning site, so that the PUP1 cDNA from this vector can be isolated as a KpnI-XbaI fragment. This 1.2 kb fragment was cloned in the KpnI-XbaI excised vector pBinAR, a derivative of pBIN19 (Bevan, 1984, *Nucl. Acids Res.* 12, 8711–8720). The resulting plasmid was named p35S-PUP1.
b) Anti-sense repression: from the plasmid pFL61-PUP1 a 1.1 kb-sized HpaI-SspI-PUP1 fragment was isolated and cloned in anti-sense orientation in the SmaI incision site of pBinAR. The orientation of the fragment was checked by restriction splitting. The resulting plasmid was named p35-α-PUP1.

Figure 6A:
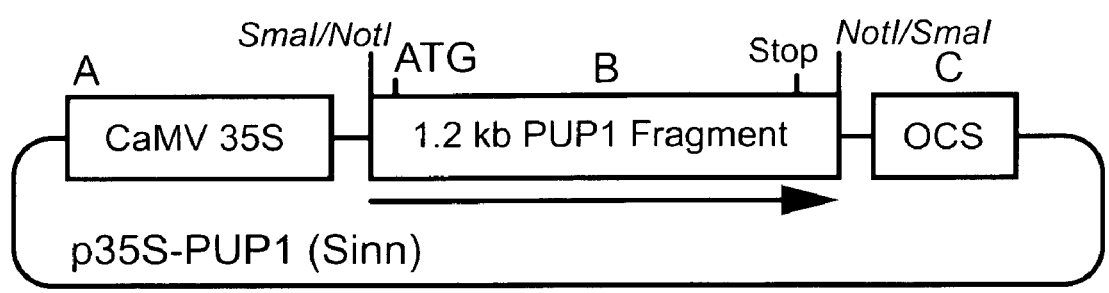
FIG. 6a shows a schematic representation of the plasmid p35S-PUP1, a derivative of the plasmid pBIN19 (Bevan, 1984, *Nucl. Acids Res.* 12, 8711–8721). A stands for a fragment from the genome of the cauliflower mosaic virus, which carries the 35S promoter (nt 6909–7437). The promoter fragment was prepared as EcoRI/KpnI fragment from the plasmid pDH51 (Pietrzak et al., *Nucl. Acids Res.* 14, 5857–5868). B stands for a NotI/NotI fragment of cDNA, flanked by a polylinker region from pT7T3/NotI with KpnI and XbaI division sites with the coding region of the nuclear base transporter of *Arabidopsis thaliana* in sense orientation to fragment A. The arrow shown in fragment B indicates the reading direction of the cDNA. C stands for a polyadenylation signal of gene 3 of the T-DNA of plasmid pTiACH5 (Gielen et al., 1984 *EMBO J*, 3, 835–846). Nucleotides 11749 to 11939, which as PvuII/HindIII fragment was isolated from the plasmid pAGV40 (Herrera-Estrella et al., 1983, *Natur*, 303, 209–213) and cloned after addition of a SphI linker to the PvuII restriction site between the SphI and HindIII cleavage sites of the polylinker of pBIN19.
Figure 6B:
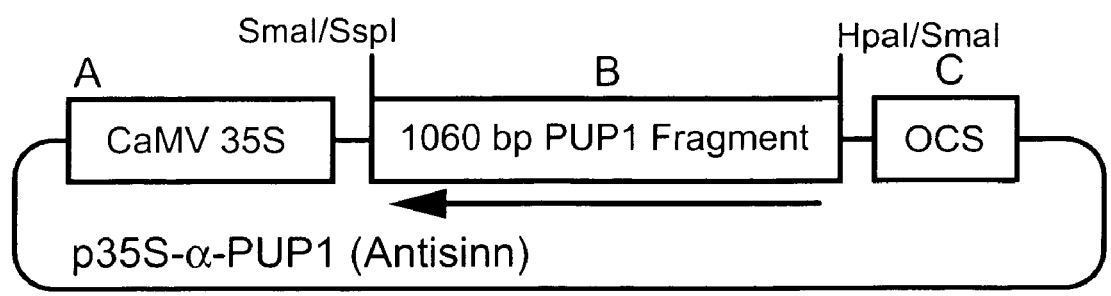
FIG. 6b shows a schematic representation of the plasmid p35S-α-PUP1, a derivative of the plasmid pBIN19 (Bevan, 1984. *Nucl. Acids Res*, 12, 8711–8721). A and C in either case stand for the CaMV35S promoter and the polyadenylation signal of gene 3 of the T-DNA of the plasmid pTiACH5 (see FIG. 6a). B stands for a SspI/HpaI fragment of the cDNA with the coding region of the nuclear base transporter of *Arabidopsis thaliana* in anti-sense orientation to fragment A. The arrow shown in fragment B indicates the reading direction of the cDNA.

The PUP1-cDNA fragments bear the designation "B" in FIGS. 6a and 6b. Whatever the case, whether B was incorporated in sense orientation to the CaMV-35S promoter of pBinAR or not, the resulting plasmid carries the designation p35S-PUP1 or p35S-α-PUP1. Between their EcoRI and KpnI excision sites a fragment from the genome of the cauliflower mosaic virus which carries the 35S promoter (nt 6909–7437) is inserted. The promoter fragment is prepared as an EcoRI/KpnI fragment from the plasmid pDH51 (Pietrzak et al., *Nucl. Acids Res.* 14, 5857–5868). In the plasmid map the promoter fragment bears the designation "A". Between the SphI and HindIII excision sites of pBinAR is inserted in addition the polyadenylation signal of gene 3 of the T-DNA of the plasmid pTiACHS (Gielen et al., *EMBO J.* 3, 835–846). For this purpose a PvuII/HindIII fragment (nt 1749–11939) from the plasmid pAGV 40 (Herrera-Estrella et al., 1983. *Nature* 303, 209–2139) had a SphI linker attached at the PvuII excision site. The polyadenylation signal carries the designation "C" in the plasmid map.

Following transformation of *agrobacteria* with the plasmids p35S-PUP1 and p35S-α-PUP1 these were put into the vacuum filtration of *Arabidopsis thaliana*.

Ten independently obtained transformants for both constructs, in which the presence of the intact, not rearranged, chimerical genes had been demonstrated with the aid of "Southern Blot" analyses, were investigated in connection with the changes in nuclear base transport.

Example 4

Expression of the PUP1 Gene in *Xenopus oocytes*

The cDNA for PUP1 was excised with NotI and cloned in an oocyte expression vector containing untranslated 5' and 3' regions of the β-globin from *Xenopus*. The cDNA was then replicated by means of PCR. SP6 (from the oocyte vector) was used as upstream primer, as downstream primer a primer was used which demolishes the STOP codon of PUP1 and simultaneously inserts a NotI excision site. This PCR fragment was excised by NotI and HindIII and ligated into an oocyte expression vector which in addition contains behind the NotI excision site the gene for GFP ("green fluorescent protein" from the jellyfish). In that way an open reading-frame is constructed for a fusion protein from PUP1 and GFP. By insertion of the NotI excision site a linker with three base pairs coding for alanine is constructed. The plasmid was linearized with MluI, and RNA was transcribed in vitro by means of SP6 polymerase and absorbed into water to about 1 ng/nl. Each oocyte (ripening stage 5 to 6) was injected with 50 nl. Following twenty days' incubation at 16° oocytes were placed for measurement in an appropriate measurement chamber and rinsed over with various solutions. The solutions contained: 100 mM N-methyl-D-glutamine chloride, 2 mM calcium chloride, 5 mM MES, pH 5.0 or 7.3, and corresponding concentrations of adenine.

Figure 7:
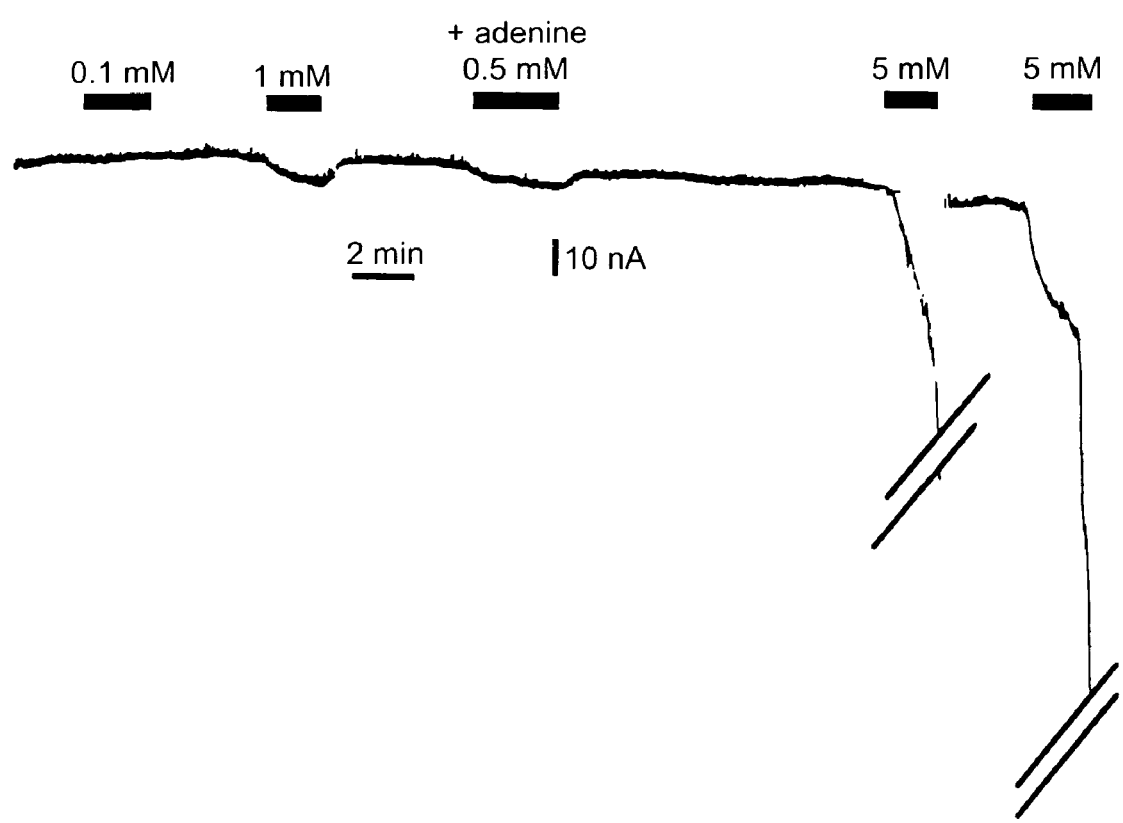
FIG. 7 shows the measurement of one-way directed currents at a constant voltage of −80 mV expressing PUP1 in *Xenopus* oocytes. The one-way directed currents are measured as soon as adenine is added. The current strength is dependent on the concentration (bars indicate the current on the ordinate and the time on the abscissa).

For voltage measurement a glass electrode filled with 3M KCl was stuck into the oocyte. With a Dagan amplifier the potential was measured relative to the reference electrode. This was connected with the bath solution via an agar bridge. In solutions without adenine at pH 7.3 oocytes had a typical resting potential of about −30 mV (see FIG. 7). Adenine in the bath solution provokes depolarization of the oocyte. This indicates that PUP1 transports adenine even in oocytes.

For measurement of current the oocytes were held at a voltage of −80 mV. Adenine in the bath solution induces a current in one direction. Since adenine itself carries no charge, that indicates a cotransport with charged ions, e.g. protons.

Example 5

PUP1-Mediated Transport of Adenosine in Yeast

The *Saccharomyces cerevisiae* strain DM734-284D (genotype: ade8-18, ade2-1, arg-4-16, leu2-17, trp1-1, lys2, ura3: Yeast Genetic Stock Center) was used for growth studies. This yeast strain owing to mutations at the gene loci ade 8-18 and ade 2-1 is not itself in a position to synthesize adenine. Hence this strain needs adenine from the external medium to be able to grow. This adenine is taken up via the purine/cytosine transporter FCY2 of the yeast. The DM734-284D strain is however still in a position to grow in medium containing adenosine instead of adenine, provided adenosine transport in the yeast cells is mediated by an adenosine transporter inserted by genetic engineering. *Saccharomyces cerevisiae* itself does not possess an adenosine transporter of such a kind. Hence the strain DM734-284D is suitable as a complementation system for the isolation of adenosine transporters from various organisms.

Figure 8:
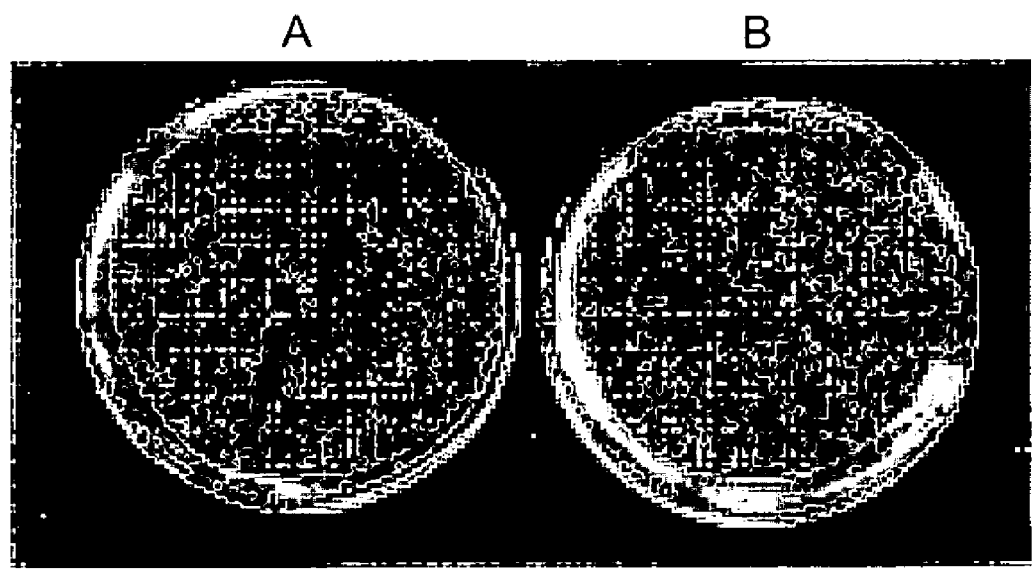
FIG. 8 shows (A) the increase of DM734-2841 DpDR195 in 150 μM adenosine (control) and (B) the increase of DM734-284DpDR195PuP1 in 150 μM adenosine.

In order to check whether PUP1 mediates the transport of adenosine, the strain DM734-284D was transformed according to the standard procedure for yeast transformation (Dohmen et al., 1991, *Yeast* 7,691–692) with the constructs pDR195PUP1 and pDR195 as controls (Rentsch et al., 1995, *FEBS Lett.* 370, 4–238). For final checking of the transformation the early stages of transformation were plated on minimal medium containing 150 μM adenine and the amino acids arginine, leucine, tryptophane (each 60 mg/l) and lysine (70 mg/l) necessary for growth. Uracil served as transformation marker. Three independent positive clones of the control and the PUP1-expressing clone were plated on minimal medium containing 150 μM adenosine instead of 150 μM adenine. Definite growth was shown after 3 days by the PUP1-expressing clone, while the clone transformed with the vector pDR195 showed no growth (see FIG. 8). This indicates that PUP1 mediates the transport of the nucleoside and adenine-derivative adenosine.

Example 6

PUP1-Mediated Transport of Caffeine in Yeast

In order to check whether PUP1 mediates the transport of caffeine, the sensitivity of the *Saccharomyces cerevisiae* strain MG887ura3⁻ to caffeine-containing minimal medium was investigated. At certain concentrations caffeine is toxic to yeast (Bard et al., *J. Bacteriol.* 141, 999–1002), leading to slower growth or death of the yeast. If PUP1 mediates the transport of caffeine it may be assumed that a yeast strain expressing this protein possesses a greater sensitivity to caffeine, manifested as reduced growth, than the corresponding control strain.

Figure 9:
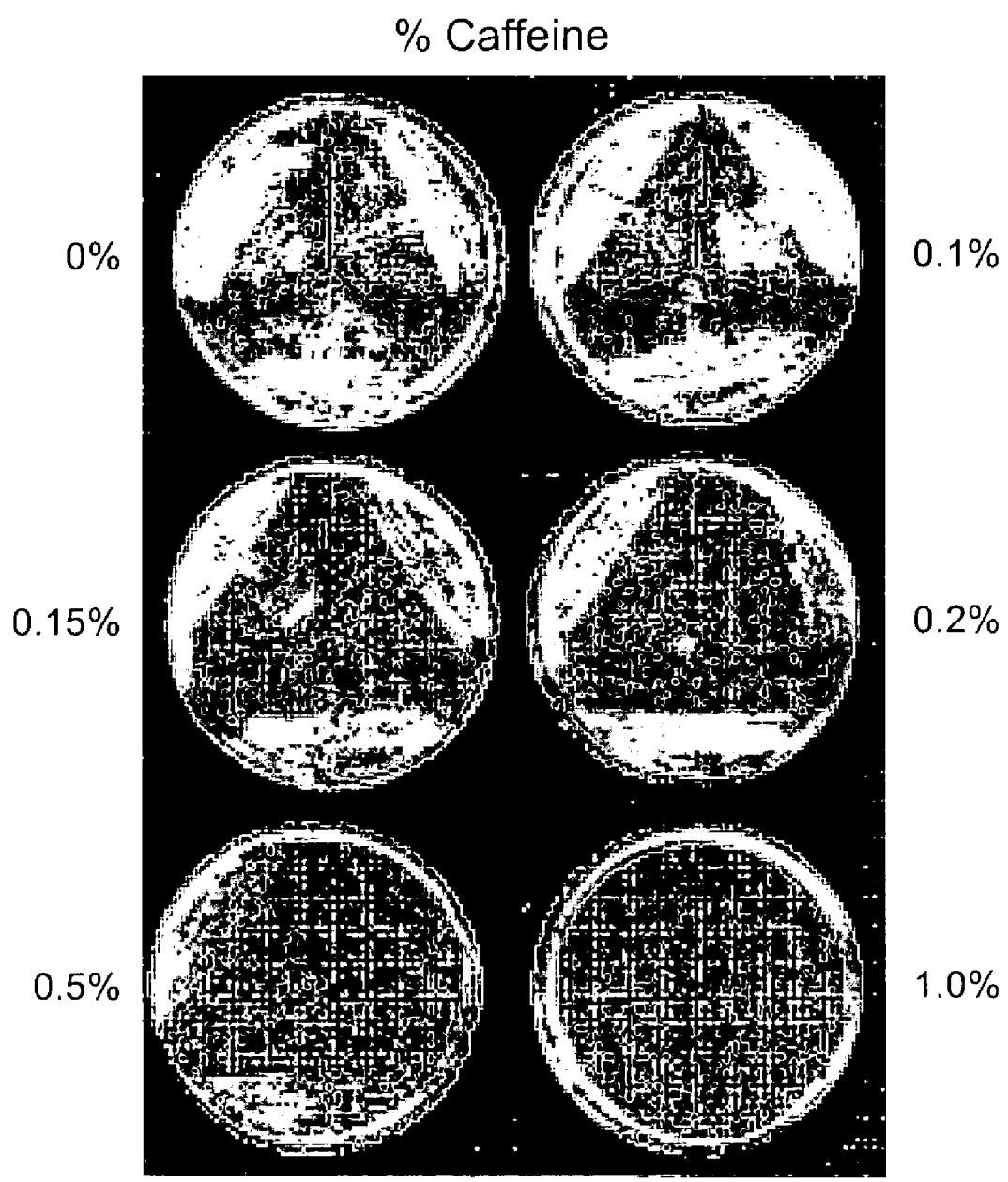
FIG. 9 shows the growth of *Saccharomyces cerevisiae* MG877ura3⁻(K) and transformed clones with the construct pDR195PUP1 (1) or with the construct pDR195PUP2 on caffeine plates with various caffeine concentrations.

For this test various caffeine concentrations between 0 and 1.5% were put into minimal medium. Yeast clones grown in liquid minimal medium for 16 hours were spread out on the corresponding plates and incubated for 6 days at 28° C. It was indicated by this that PUP1-expressing yeasts displayed distinctly slowed-down growth compared to the control strain MG877ura3⁻ and the PUP2-expressing strain from the concentration of 0.2% caffeine on (see FIG. 9). This must be ascribed to the increased uptake of toxic caffeine and shows that PUP1 mediates the transport of caffeine.

What is claimed is:

1. An isolated nucleic acid that encodes a nuclear base transporter comprising the amino acid sequence as set forth in SEQ ID NO: 8.

2. The nucleic acid of claim 1, wherein the nucleic acid comprises the nucleic acid sequence as set forth in SEQ ID NO: 1.

3. An isolated nucleic acid that encodes a nuclear base transporter and comprises the sequence as set forth in SEQ ID NO: 2.

4. The nucleic acid of claim 1, wherein the nucleic acid is a DNA molecule.

5. A DNA construct comprising the nucleic acid of claim 1 or 3.

6. The DNA construct of claim 5, wherein the construct is a plasmid.

7. A host cell comprising the DNA construct of claim 5.

8. The host cell of claim 7, wherein the host cell is selected from the group consisting of bacterial cells, yeast cells and plant cells.

9. A transgenic plant, transgenic plant part, or transgenic seed of the transgenic plant, each comprising the isolated nucleic acid of claim 1 or claim 3.

10. A process for producing a transgenic plant comprising:
   a) inserting the nucleic acid of claim 1 or claim 3 into a plant cell to make a transformed plant cell; and
   b) regenerating a transformed plant from the transformed plant cell.

11. A process for influencing expression of a nuclear base transporter in a plant cell or plant, comprising inserting into the plant cell or plant the nucleic acid of claim 1 or claim 3.

12. A method for the expression of a nuclear base transporter in a prokaryotic or eukaryotic cell, comprising transfecting said cell with the DNA construct of claim 5 under conditions that the nuclear base transporter is expressed.

13. The transgenic plant, transgenic plant part, or transgenic seed of claim 9, wherein said nucleic acid is under the control of a regulatory sequence.

14. A transgenic plant cell produced by the process of claim 11.

15. A transgenic plant produced by the process of claim 11.

16. A method of producing a transformed plant comprising regenerating a plant from the transformed plant cell of claim 14.

17. The isolated nucleic acid of claim 1 or 3, wherein the nucleic acid complements a yeast cell that is deficient in fcy2 expression.

18. The isolated nucleic acid of claim 1 or 3, wherein the nuclear base transporter transports at least one compound selected from the group consisting of nuclear bases, nucleosides, cytokinins and alkaloids.

19. The isolated nucleic acid of claim 18, wherein the nuclear bases are selected from the group consisting of adenine, cytosine and hypoxanthine.

20. The isolated nucleic acid of claim 18, wherein the nucleosides are selected from the group consisting of adenosine and cytidine.

21. The isolated nucleic acid of claim 18, wherein the cytokinins are selected from the group consisting of zeatine and kinetine.

22. An isolated nucleic acid comprising the complement of the nucleic acid of SEQ ID NO: 1 or the complement SEQ ID NO: 2.

23. A DNA construct comprising the nucleic acid of claim 22.

24. The DNA construct of claim 23, wherein the construct is a plasmid.

25. A method for inhibiting the expression of an endogenous nuclear base transporter in a plant cell comprising inserting into said cell the isolated nucleic acid of claim 22.

* * * * *